US005489678A

United States Patent [19]

Fodor et al.

[11] Patent Number: 5,489,678

[45] Date of Patent: Feb. 6, 1996

[54] PHOTOLABILE NUCLEOSIDE AND PEPTIDE PROTECTING GROUPS

[75] Inventors: Stephen P. A. Fodor, Palo Alto; Lubert Stryer, Stanford; James L. Winkler, Palo Alto; Christopher P. Holmes, Sunnyvale; Dennis W. Solas, San Francisco, all of Calif.

[73] Assignee: Affymax Technologies N.V., Curaco, Netherlands

[21] Appl. No.: 390,272

[22] Filed: Feb. 16, 1995

Related U.S. Application Data

[63] Continuation of Ser. No. 624,120, Dec. 6, 1990, abandoned, which is a continuation-in-part of Ser. No. 492,462, Mar. 7, 1990, Pat. No. 5,143,854, which is a continuation-in-part of Ser. No. 362,901, Jun. 7, 1989, abandoned.

[51] Int. Cl.[6] .......................... C07H 21/00; C07H 21/02; C07H 21/04

[52] U.S. Cl. .......................................... 536/22.1; 536/23.1

[58] Field of Search .................................... 536/22.1, 23.1

[56] References Cited

U.S. PATENT DOCUMENTS

| | | | |
|---|---|---|---|
| 4,269,933 | 5/1981 | Pazos | 430/291 |
| 4,516,833 | 5/1985 | Fusek | 350/162.12 |
| 4,562,157 | 12/1985 | Lowe et al. | 435/291 |
| 4,704,353 | 11/1987 | Humpries et al. | 435/4 |
| 4,713,326 | 12/1987 | Dattagupta et al. | 435/6 |
| 4,811,062 | 3/1989 | Tabata et al. | 356/152 |
| 4,833,092 | 5/1989 | Geysen | 436/501 |
| 4,846,552 | 7/1989 | Veldkamp et al. | 350/162.2 |
| 4,946,942 | 8/1990 | Fuller et al. | 530/335 |
| 4,981,985 | 1/1991 | Kaplan et al. | 556/50 |
| 4,984,100 | 1/1991 | Takayama et al. | 360/49 |
| 5,079,600 | 1/1992 | Schnur et al. | 357/4 |
| 5,143,854 | 9/1992 | Pirrung et al. | 436/518 |
| 5,252,743 | 10/1993 | Barrett et al. | 548/303.7 |
| 5,258,506 | 11/1993 | Urdea et al. | 536/23.1 |

FOREIGN PATENT DOCUMENTS

| | | | |
|---|---|---|---|
| 0046083 | 2/1982 | European Pat. Off. | B01F 17/00 |
| 0392546 | 4/1990 | European Pat. Off. | C12Q 1/68 |
| 0103197 | 3/1984 | European Pat. Off. | C07C 79/46 |
| 2196476 | 2/1990 | United Kingdom . | |
| 8606487 | 11/1986 | WIPO | G01N 33/53 |
| 8910977 | 11/1989 | WIPO | C12Q 1/68 |
| 8911548 | 11/1989 | WIPO | C12Q 1/68 |
| 9003382 | 4/1990 | WIPO | C07H 21/00 |
| 9004652 | 5/1990 | WIPO | C12Q 1/68 |
| 9410128 | 5/1994 | WIPO | C07C 205/06 |

OTHER PUBLICATIONS

Gurney et al, *Activation of a Potassium Current by Rapid Photochemically Generated Step Increases of Intracellular Calcium in Rat Sympathetic Neurons,* Proc. Natl. Acad. Sci. USA 84:3496–3500, (May 1987).

Tsien et al., *Control of Cytoplasmic Calcium with Photolabile Tetracarboxylate 2–Nitrobenzhydrol Chelators,* Biophys. J. 50:843–853, (Nov. 1986).

Kaplan et al., *Photolabile Chelators for the Rapid Photorelease of Divalent Cations,* Proc. Natl. Acad. Sci. USA 85:6571–6575, (Sep. 1988).

Adams et al., *Photolabile Chelators That "Cage" Calcium with Improved Speed of Release and Pre–Photolysis Affinity,* J. General Physiology, (Dec. 1986). Abstract.

B. Amit et al., *Photosensitive Protecting Groups–A Review,* Israel J of Chemistry vol. 12 Nos. 1–2:103–113 (1974).

Furka et al., *Int. J. Peptide Protein Res.* (1991) 37:487–493.

Furka et al., Abstract No. FR:013 from *14th Int'l Congress of Biochem.,* Prague, Czechoslovakia, Jul. 10–15, 1988.

Furka et al., Abstract No. 288 from *Xth Int'l Symposium on Medicinal Chemistry,* Budapest, Hungary, Aug. 15–19, 1988.

Ohtsuka et al., *Nucleic Acids Research* (1974) 1:1351–1357.

Zehavi et al., *J. Org. Chem.* (1972) 37:2281–2285.

Lam et al., *Nature* (1991) 354:82–86.

Chung–gi Shin et al., *Dehydrooligopeptides, XI. Facile Syntheses of Various Kinds of Dehydrodi– and tripeptides, and Dehydroenkephalins Containing ΔTyr Residue by Using N–Carboxydehydrotyrosine Anhydride,* (1989) *Bull. Chem. Soc. Jpn.* 62:1127–1135.

Stephanie A. Robertson, et al., *A General and Efficient Route for Chemical Aminoacylation of Transfer RNAs,* (1991) *J. Am. Chem. Soc.* 113:2722–2729.

Michiko Iwamura et al., 1–(α–Diazobenzyl)pyrene: A Reagent for Photolabile and Fluorescent Protection of Carboxyl Groups of Amino Acids and Peptides, (1991) *Synlett* 35–36.
Cameron et al., *Photogneration of Organic Bases from o–Nitrobenzyl–Derived Carbamates, J. Am. Chem. Soc. (1991) 113, 4303–4313.*
V. N. Rajasekharan Pillai, *3–Nitro–4–Aminomethylbenzoylderivate von Poly–ethylenglykolen: Eine neue Klasse von Photosensitiven löslichen Polymeren Trägern zur Synthese von C–terminalen Peptidamiden,* Tetrahedron Letters No. 36:3409–3412 (1979).
Amit et al., *Photosensitive Protecting Groups of Amino Sugars and Their Use in Glycoside Synthesis. 2–Nitro–benzyloxycarbonylamino and 6–Nitroveratryloxycarbonylamino Derivatives,* J. Org. Chem. 39:192–196 (1974).
Reichmanis et al., *The efficiency of various 2–nitrobenzyl groups . . . ,* J. Polymer Sc. Polymer Chem. Ed. 23:1–8 (1985).
McCray et al., *Properties and Uses of Photoreactive Caged Compounds,* Annu. Rev. Biophys. Biophys. Chem. 18:239–70 (1989).
J. A. Barltrop et al., *Photosensitive Protective Groups,* Chemical Communications, p. 822 (Nov. 22, 1966).
Wilcox et al., "Synthesis of photolabile 'precursors' of amino acid neurotransmitters," *J. Org. Chem.* 55:1585–1589 (1990).
Craig et al., 1990, Nucl. Acids Res. 18(9):2653–2659. Ordering of cosmid clones covering the Herpes simples is type 1 (HSV–1) genome:a test case for fingerprinting by hybridization.
Dulcey et al., 26 Apr. 1991, Science 252:551–554. Deep UV Photochemistry of Chemisorbed Monolayers: Patterned Coplanar Molecular Assemblies.
Haridasan et al., 1987, Proc. Indian Natl. Acad. Sci. 53A (6):717–728 Peptide synthesis using photolytically cleavable 2–nitrobenzyloxycarbonyl protecting group.
Cummings et al., 1988, Tetrahedron Ltrs. 29(1):65–68 Photoactiveable 1–luorophores. 1. Synthesis and photoactivation of o–Nitrobenzyl–Quenched Fluorescent carbamates.
Iwamura et al., 1987, Tetrahedron Ltrs. 28(6):679–682 1–Pyrenylmethyl Esters, Photolabile Protecting Groups For Carboxylic Acids.
Poustka et al., 1986, CSH Symp. Quant. Biol. 51:131–139 Molecular approaches to mammalian genetics.
Bains et al., 1988, J. Theor. Biol. 135:303–307 A Novel Method for Nucleic Acid Sequence Determination.
Lysov et al., Dec. 1988, Translation from Dok. Akad. Nauk SSSR 303 (6)1508–1511 A new method for determining the DNA nucleotide sequence by hybridization with oligonucleotides.
Khrapko et al., Oct. 1989, FEBS Ltrs. 256 (1,2):118–122 An oligonucleotide hybridization approach to DNA sequencing.
Drmanac et al., 1989, Genomics 4:114–128 Sequencing of megabase plus DNA by hybridization: Theory of the method.
L.R., 2 Dec. 1988, Science 242:1245 A Sequencing Rality Check.
Logue et al., 19–20 Jan. 1989, SPIE 1052:19–24 General approaches to mask design for binary optics.
Krile et al., 1 Jan. 1979, Applied Optics 18(1):52–56 Multiplex holography with chirp–modulated binary phase–coded reference–beam masks.
Veldkamp., 21 May 1990, CLEO:30–32 (paper No. CMG6) Binary Optics: the optics technology of the 1990's.
1 Feb. 1990, Biotechnology News 10(3):7–8 Affymax raises $25 million to develop high–speed drug discovery system.
Fodor et al., 1991, Research Article, 251:767–773 Light–directed, spatially addressable parallel chemical synthesis.
Patent Abstracts of Japan from the EPO, Abst. vol. 13:557, pub. date Dec. 28, 1989 abstracting Japanese Patent 1–233447.
Schupp et al., *Mechanistic Studies of the Photorearrangement of o–Nitrobenzyl Esters,* J. of Photochem. 36:85–97 (1987).
Adams et al., *Biologically Useful Chelators That Take Up* $Ca^{2+}$ upon Illumination, J. Am. Chem. Soc. 111:7957–7968 (1989).
Walker et al., *Photolabile Protecting Groups for an Acetyl–choline Receptor Ligand. Synthesis and Photochemistry of a new Class of o–Nitrobenzyl Derivatives and Their Effects on Receptor Function,* Biochemistry 25:1799–1805 (1986).
Baldwin et al., *New Photolabile Phosphate Protecting Groups,* Tetrahedron vol. 46, No. 19:6879–6884 (1990).
V. N. Rajasekharan Pillai, *Photoremovable Protecting Groups in Organic Synthesis,* Synthesis pp. 1–26 (Jan. 1980).
Reichmanis, E., et al., "o–Nitrobenzyl Photochemistry: Solution vs. Solid–State Behavior", *J. Polymer Science,* 23(1):1–8 (1985).
Kleinfeld et al., "Controlled Outgrowth of Dissociated Neurons on Patterned Substrates," *J. of Neuroscience,* 8(11):4098–4120, Nov. 1988.

*Primary Examiner*—W. Gary Jones
*Assistant Examiner*—David Schreiber
*Attorney, Agent, or Firm*—Townsend and Townsend and Crew

[57] ABSTRACT

A synthetic strategy for the creation of large scale chemical diversity. Solid-phase chemistry, photolabile protecting groups, and photolithography are used to achieve light-directed spatially-addressable parallel chemical synthesis. Binary masking techniques are utilized in one embodiment. A reactor system, photoremovable protective groups, and improved data collection and handling techniques are also disclosed. A technique for screening linker molecules is also provided.

35 Claims, 17 Drawing Sheets

Microfiche Appendix Included
(3 Microfiche, 226 Pages)

(3 Microfiche, 226 Pages)

PHOTOLABILE NUCLEOSIDE AND PEPTIDE PROTECTING GROUPS

This is a continuation of application Serial No. 07/624/120, filed Dec. 6, 1990, now abandoned.

CROSS REFERENCE TO RELATED APPLICATIONS

Application Ser. No. 07/624,120 was a continuation-in-part of application Ser. No. 492,462, filed Mar. 7, 1990, allowed as U.S. Pat. No. 5,143,854, which is a continuation-in-part of pending application Ser. No. 362,901, filed Jun. 7, 1989, abandoned, assigned to the assignee of the present application, and incorporated herein by reference for all purposes. This application is related to applications with Serial Nos. 07,626,730 and 07/642,114, abandoned, respectively filed on the same day as the present application, and also incorporated herein by reference for all purposes. Microfiche appendices A and B are attached, including 3 sheets of microfiche comprising 226 frames.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

The present invention relates to the field of polymer synthesis. More specifically, the invention provides a reactor system, a masking strategy, photoremovable protective groups, data collection and processing techniques, and applications for light directed synthesis of diverse polymer sequences on substrates.

SUMMARY OF THE INVENTION

Methods, apparatus, and compositions for synthesis and use of diverse polymer sequences on a substrate are disclosed, as well as applications thereof.

According to one aspect of the invention, an improved reactor system for synthesis of diverse polymer sequences on a substrate is provided. According to this embodiment the invention provides for a reactor for contacting reaction fluids to a substrate; a system for delivering selected reaction fluids to the reactor; a translation stage for moving a mask or substrate from at least a first relative location relative to a second relative location; a light for illuminating the substrate through a mask at selected times; and an appropriately programmed digital computer for selectively directing a flow of fluids from the reactor system, selectively activating the translation stage, and selectively illuminating the substrate so as to form a plurality of diverse polymer sequences on the substrate at predetermined locations.

The invention also provides a technique for selection of linker molecules in a very large scale immobilized polymer synthesis VLSIPS™method. According to this aspect of the invention, the invention provides a method of screening a plurality of linker polymers for use in binding affinity studies. The invention includes the steps of forming a plurality of linker polymers on a substrate in selected regions, the linker polymers formed by the steps of recursively: on a surface of a substrate, irradiating a portion of the selected regions to remove a protective group, and contacting the surface with a monomer; contacting the plurality of linker polymers with a ligand; and contacting the ligand with a labeled receptor.

According to another aspect of the invention, improved photoremovable protective groups are provided. According to this aspect of the invention a compound having the formula:

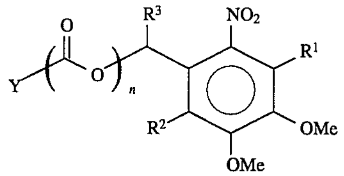

wherein n=0 or 1; Y is selected from the group consisting of an oxygen of the carboxyl group of a natural or unnatural amino acid, an amino group of a natural or unnatural amino acid, or the C—5' oxygen group of a natural or unnatural deoxyribonucleic or ribonucleic acid; $R^1$ and $R^2$ independently are a hydrogen atom, a lower alkyl, aryl, benzyl, halogen, hydroxyl, alkoxyl, thiol, thioether, amino, nitro, carboxyl, formate, formamido, sulfido, or phosphido group; and $R^3$ is a alkoxy, alkyl, aryl, hydrogen, or alkenyl group is provided.

The invention also provides improved masking techniques for the VLSIPS™ methodology. According to one aspect of the masking technique, the invention provides an ordered method for forming a plurality of polymer sequences by sequential addition of reagents comprising the step of serially protecting and deprotecting portions of the plurality of polymer sequences for addition of other portions of the polymer sequences using a binary synthesis strategy.

Improved data collection equipment and techniques are also provided. According to one embodiment, the instrumentation provides a system for determining affinity of a receptor to a ligand comprising: means for applying light to a surface of a substrate, the substrate comprising a plurality of ligands at predetermined locations, the means for providing simultaneous illumination at a plurality of the predetermined locations; and an array of detectors for detecting light fluoresced at the plurality of predetermined locations. The invention further provides for improved data analysis techniques including the steps of exposing fluorescently labelled receptors to a substrate, the substrate comprising a plurality of ligands in regions at known locations; at a plurality of data collection points within each of the regions, determining an amount of light fluoresced from the data collection points; removing the data collection points deviating from a predetermined statistical distribution; and determining a relative binding affinity of the receptor to remaining data collection points.

Protected amino acid N-carboxy anhydrides for use in polymer synthesis are also disclosed. According to this aspect, the invention provides a compound having the formula:

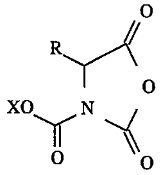

where R is a side chain of a natural or unnatural amino acid and X is a photoremovable protecting group.

A further understanding of the nature and advantages of the inventions herein may be realized by reference to the remaining portions of the specification and the attached drawings.

DESCRIPTION OF THE PREFERRED EMBODIMENTS

CONTENTS

Figure 1:
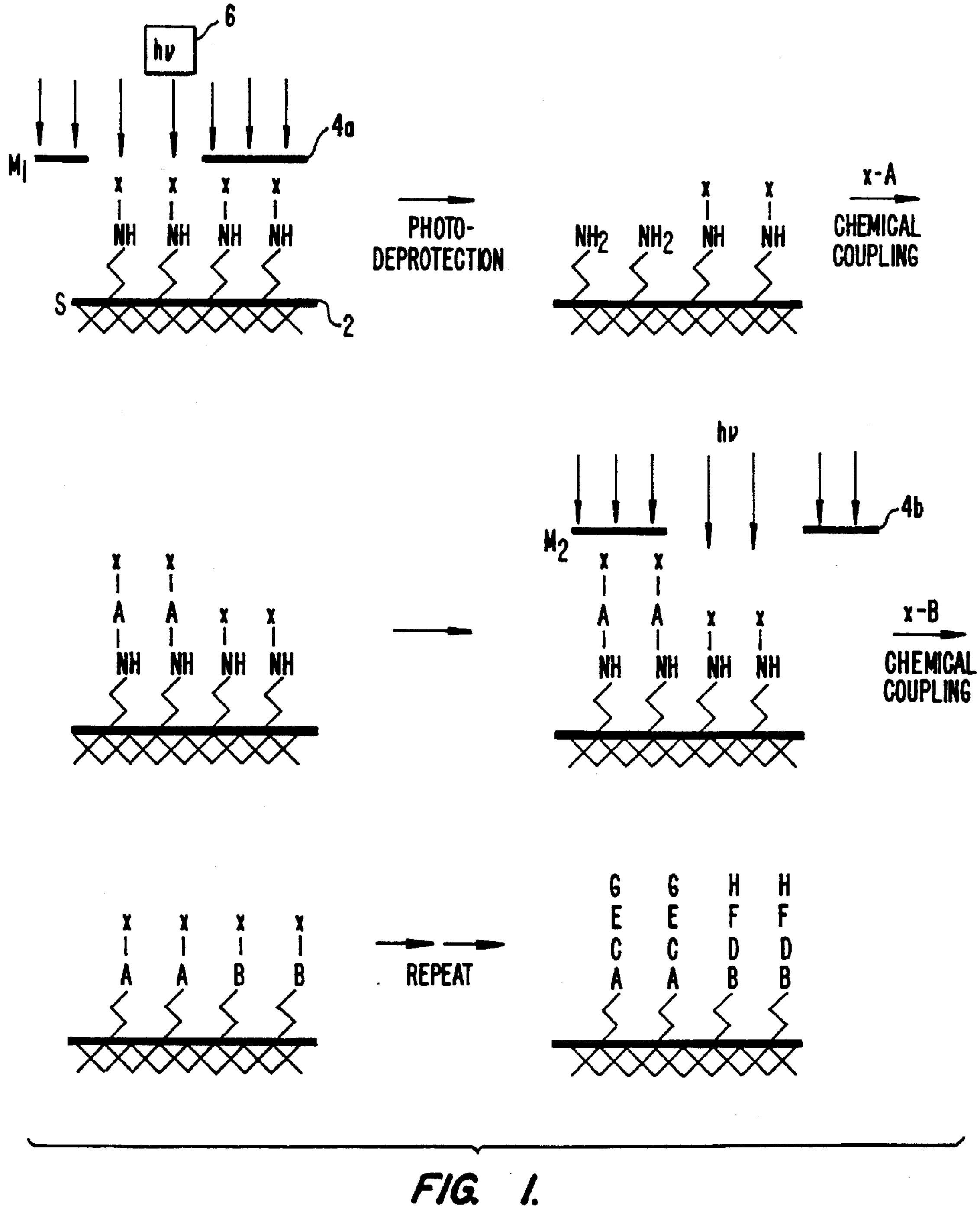
FIG. 1 schematically illustrates light-directed spatially-addressable parallel chemical synthesis.

I. Definitions
II. General
A. Deprotection and Addition
1. Example
2. Example
B. Antibody recognition
1. Example
III. Synthesis
A. Reactor System
B. Binary Synthesis Strategy
1. Example
2. Example
3. Example
4. Example
5. Example
6. Example
C. Linker Selection
D. Protecting Groups
1. Use of Photoremovable Groups During Solid-Phase Synthesis of Peptides
2. Use of Photoremovable Groups During Solid-Phase Synthesis of Oligonucleotides
E. Amino Acid N-Carboxy Anhydrides Protected with a Photoremovable Group
IV. Data Collection
A. Data Collection System
B. Data Analysis
V. Other Representative Applications
A. Oligonucleotide Synthesis
1. Example
VI. Conclusion I. Definitions Certain terms used herein are intended to have the following general definitions:

1. Complementary: Refers to the topological compatibility or matching together of interacting surfaces of a ligand molecule and its receptor. Thus, the receptor and its ligand can be described as complementary, and furthermore, the contact surface characteristics are complementary to each other.

2. Epitope: The portion of an antigen molecule which is delineated by the area of interaction with the subclass of receptors known as antibodies.

3. Ligand: A ligand is a molecule that is recognized by a particular receptor. Examples of ligands that can be investigated by this invention include, but are not restricted to, agonists and antagonists for cell membrane receptors, toxins and venoms, viral epitopes, hormones hormone receptors, peptides, enzymes, enzyme substrates, cofactors, drugs (e.g., opiates, steroids, etc.), lectins, sugars, oligonucleotides, nucleic acids, oligosaccharides, proteins, and monoclonal antibodies.

4. Monomer: A member of the set of small molecules which can be joined together to form a polymer. The set of monomers includes but is not restricted to, for example, the set of common L-amino acids, the set of D-amino acids, the set of synthetic amino acids, the set of nucleotides and the set of pentoses and hexoses. As used herein, monomers refers to any member of a basis set for synthesis of a polymer. For example, dimers of the 20 naturally occurring L-amino acids form a basis set of 400 monomers for synthesis of polypeptides. Different basis sets of monomers may be used at successive steps in the synthesis of a polymer. Furthermore, each of the sets may include protected members which are modified after synthesis.

5. Peptide: A polymer in which the monomers are alpha amino acids and which are joined together through amide bonds and alternatively referred to as a polypeptide. In the context-of this specification it should be appreciated that the amino acids may be the L-optical isomer or the D-optical isomer. Peptides are often two or more amino acid monomers long, and often more than 20 amino acid monomers long. Standard abbreviations for amino acids are used (e.g., P for proline). These abbreviations are included in Stryer, *Biochemistry,* Third Ed., 1988, which is incorporated herein by reference for all purposes.

6. Radiation: Energy which may be selectively applied including energy having a wavelength of between $10^{-14}$ and $10^{4}$ meters including, for example, electron beam radiation, gamma radiation, x-ray radiation, ultra-violet radiation, visible light, infrared radiation, microwave radiation, and radio waves. "Irradiation" refers to the application of radiation to a surface.

7. Receptor: A molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex.

Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance one type of receptor includes, the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides are described in, for example, U.S. Pat. No. 4,215,899, which is incorporated herein by reference for all purposes.

f) Hormone receptors: Examples of hormone receptors include, e.g., the receptors for insulin and growth hormone. Determination of the ligands which bind with high affinity to a receptor is useful in the development of, for example, an oral replacement of the daily injections which diabetics must take to relieve the symptoms of diabetes, and in the other case, a replacement for the scarce human growth hormone which can only be obtained from cadavers or by recombinant DNA technology. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

8. Substrate: A material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or the like. According to other embodiments, small beads may be provided on the surface which may be released upon completion of the synthesis.

9. Protective Group: A material which is chemically bound to a monomer unit and which may be removed upon selective exposure to an activator such as electromagnetic radiation. Examples of protective groups with utility herein include those comprising nitropiperonyl, pyrenylmethoxy-carbonyl, nitroveratryl, nitrobenzyl, dimethyl dimethoxy-benzyl, 5-bromo-7-nitroindolinyl, o-hydroxy-α-methyl cinnamoyl, and 2-oxymethylene anthraquinone.

10. Predefined Region: A predefined region is a localized area on a surface which is, was, or is intended to be activated for formation of a polymer. The predefined region may have any convenient shape, e.g., circular, rectangular, elliptical, wedgeshaped, etc. For the sake of brevity herein, "predefined regions" are sometimes referred to simply as "regions."

11. Substantially Pure: A polymer is considered to be "substantially pure" within a predefined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor.

12. Activator refers to an energy source adapted to render a group active and which is directed from a source to a predefined location on a substrate. A primary illustration of an activator is light. Other examples of activators include ion beams, electric fields, magnetic fields, electron beams, x-ray, and the like.

13. Binary Synthesis Strategy refers to an ordered strategy for parallel synthesis of diverse polymer sequences by sequential addition of reagents which may be represented by a reactant matrix, and a switch matrix, the product of which is a product matrix. A reactant matrix is a $1\times n$ matrix of the building blocks to be added. The elements of the switch matrix are binary numbers. In preferred embodiments, a binary strategy is one in which at least two successive steps illuminate half of a region of interest on the substrate. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme, but will still be considered to be a binary masking scheme within the definition herein. A binary "masking" strategy is a binary synthesis which uses light to remove protective groups from materials for addition of other materials such as amino acids. In preferred embodiments, selected columns of the switch matrix are arranged in order of increasing binary numbers in the columns of the switch matrix.

14. Linker refers to a molecule or group of molecules attached to a substrate and spacing a synthesized polymer from the substrate for exposure/binding to a receptor.

II. General

The present invention provides synthetic strategies and devices for the creation of large scale chemical diversity.

Solid-phase chemistry, photolabile protecting groups, and photolithography are brought together to achieve light-directed spatially-addressable parallel chemical synthesis in preferred embodiments.

The invention is described herein for purposes of illustration primarily with regard to the preparation of peptides and nucleotides, but could readily be applied in the preparation of other polymers. Such polymers include, for example, both linear and cyclic polymers of nucleic acids, polysaccharides, phospholipids, and peptides having either α-, β-, or ω-amino acids, hetero-polymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure. It will be recognized further, that illustrations herein are primarily with reference to C- to N-terminal synthesis, but the invention could readily be applied to N- to C-terminal synthesis without departing from the scope of the invention.

A. Deprotection and Addition

The present invention uses a masked light source or other activator to direct the simultaneous synthesis of many different chemical compounds. FIG. 1 is a flow chart illustrating the process of forming chemical compounds according to one embodiment of the invention. Synthesis occurs on a solid support 2. A pattern of illumination through a mask 4a using a light source 6 determines which regions of the support are activated for chemical coupling. In one preferred embodiment activation is accomplished by using light to remove photolabile protecting groups from selected areas of the substrate.

After deprotection, a first of a set of building blocks (indicated by "A" in FIG. 1), each bearing a photolabile protecting group (indicated by "X") is exposed to the surface of the substrate and it reacts with regions that were addressed by light in the preceding step. The substrate is then illuminated through a second mask 4b, which activates another region for reaction with a second protected building block "B". The pattern of masks used in these illuminations and the sequence of reactants define the ultimate products and their locations, resulting in diverse sequences at predefined locations, as shown with the sequences ACEG and BDFH in the lower portion of FIG. 1. Preferred embodiments of the invention take advantage of combinatorial masking strategies to form a large number of compounds in a small number of chemical steps.

A high degree of miniaturization is possible because the density of compounds is determined largely with regard to spatial addressability of the activator, in one case the diffraction of light. Each compound is physically accessible and its position is precisely known. Hence, the array is spatially-addressable and its interactions with other molecules can be assessed.

In a particular embodiment shown in FIG. 1, the substrate contains amino groups that are blocked with a photolabile protecting group. Amino acid sequences are made accessible for coupling to a receptor by removal of the photoprotective groups.

When a polymer sequence to be synthesized is, for example, a polypeptide, amino groups at the ends of linkers attached to a glass substrate are derivatized with nitroveratryloxycarbonyl (NVOC), a photoremovable protecting group. The linker molecules may be, for example, aryl acetylene, ethylene glycol oligomers containing from 2–10 monomers, diamines, diacids, amino acids, or combinations thereof. Photodeprotection is effected by illumination of the substrate through, for example, a mask wherein the pattern has transparent regions with dimensions of, for example, less than 1 $cm^2$, $10^{-1}$ $cm^2$, $10^{-2}$ $cm^2$, $10^{-3}$ $cm^2$, $10^{-4}$ $cm^2$, $10^{-5}$ $cm^2$, $10^{-6}$ $cm^2$, $10^{-7}$ $cm^2$, $10^{-8}$ $cm^2$, or $10^{-10}$ $cm^2$. In a preferred embodiment, the regions are between about 10×10 µm and 500×500 µm. According to some embodiments, the masks are arranged to produce a checkerboard array of polymers, although any one of a variety of geometric configurations may be utilized.

1. Example

In one example of the invention, free amino groups were fluorescently labelled by treatment of the entire substrate surface with fluorescein isothiocynate (FITC) after photodeprotection. Glass microscope slides were cleaned, aminated by treatment with 0.1% aminopropyltriethoxysilane in 95% ethanol, and incubated at 110° C. for 20 min. The aminated surface of the slide was then exposed to a 30 mM solution of the N-hydroxysuccinimide ester of NVOC-GABA (nitroveratryloxycarbonyl-τ-amino butyric acid) in DMF. The NVOC protecting group was photolytically removed by imaging the 365 nm output from a Hg arc lamp through a chrome on glass 100 µm checkerboard mask onto the substrate for 20 min at a power density of 12 $mW/cm^2$. The exposed surface was then treated with 1 mM FITC in DMF. The substrate surface was scanned in an epi-fluorescence microscope (Zeiss Axioskop 20) using 488 nm excitation from an argon ion laser (Spectra-Physics model 2025). The fluorescence emission above 520 nm was detected by a cooled photomultiplier (Hamamatsu 943-02) operated in a photon counting mode. Fluorescence intensity was translated into a color display with red in the highest intensity and black in the lowest intensity areas. The presence of a high-contrast fluorescent checkerboard pattern of 100×100 µm elements revealed that free amino groups were generated in specific regions by spatially-localized photodeprotection.

2. Example

Figure 2:
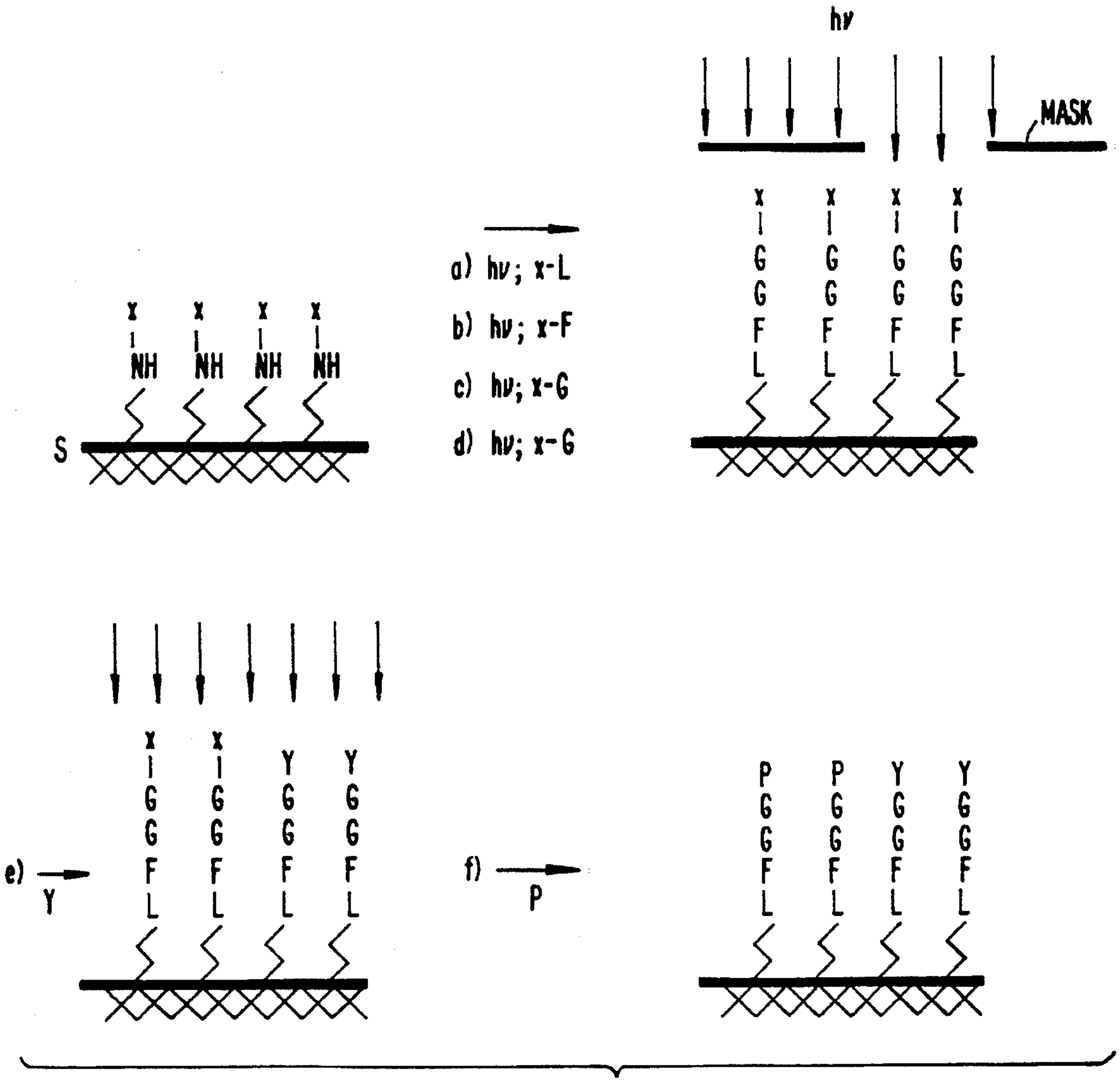
FIG. 2 schematically illustrates one example of light-directed peptide synthesis.

FIG. 2 is a flow chart illustrating another example of the invention. Carboxy-activated NVOC-leucine was allowed to react with an aminated substrate. The carboxy activated HOBT ester of leucine and other amino acids used in this synthesis was formed by mixing 0.25 mmol of the NVOC amino protected amino acid with 37 mg HOBT (1-hydroxybenzotriazole), 111 mg BOP (benzotriazolyl-n-oxy-tris (dimethylamino)-phosphoniumhexa-fluorophosphate) and 86 µl DIEA (diisopropylethylamine) in 2.5 ml DMF. The NVOC protecting group was removed by uniform illumination. Carboxy-activated NVOC-phenylalanine was coupled to the exposed amino groups for 2 hours at room temperature, and then washed with DMF and methylene chloride. Two unmasked cycles of photodeprotection and coupling with carboxy-activated NVOC-glycine were carried out. The surface was then illuminated through a chrome on glass 50 µm checkerboard pattern mask. Carboxy-activated Nα-tBOC-O-tButyl-L-tyrosine was then added. The entire surface was uniformly illuminated to photolyze the remaining NVOC groups. Finally, carboxy-activated NVOC-L-proline was added, the NVOC group was removed by illumination, and the t-BOC and t-butyl protecting groups were removed with TFA. After removal of the protecting groups, the surface consisted of a 50 µm checkerboard array of Tyr-Gly-Gly-Phe-Leu (YGGFL) (SEQ ID NO: 1) and Pro-Gly-Gly-Phe-Leu (PGGFL) (SEQ ID NO: 2).

B. Antibody Recognition

In one preferred embodiment the substrate is used to determine which of a plurality of amino acid sequences is recognized by an antibody of interest.

1. Example

In one example, the array of pentapeptides in the example illustrated in FIG. 2 was probed with a mouse monoclonal antibody directed against β-endorphin. This antibody (called 3E7) is known to bind YGGFL and YGGFM (SEQ ID NO: 21) with nanomolar affinity and is discussed in Meo et al., *Proc. Natl. Acad. Sci. USA* (1983) 80:4084, which is incorporated by reference herein for all purposes. This antibody requires the amino terminal tyrosine for high affinity binding. The array of peptides formed as described in FIG. 2 was incubated with a 2 μg/ml mouse monoclonal antibody (3E7) known to recognize YGGFL. 3E7 does not bind PGGFL. A second incubation with fluoresceinated goat anti-mouse antibody labeled the regions that bound 3E7. The surface was scanned with an epi-fluorescence microscope. The results showed alternating bright and dark 50 μm squares indicating that YGGFL and PGGFL were synthesized in geometric array determined by the mask. A high contrast (>12:1 intensity ratio) fluorescence checkerboard image shows that (a) YGGFL and PGGFL were synthesized in alternate 50 μm squares, (b) YGGFL attached to the surface is accessible for binding to antibody 3E7, and (c) antibody 3E7 does not bind to PGGFL.

Figure 3:
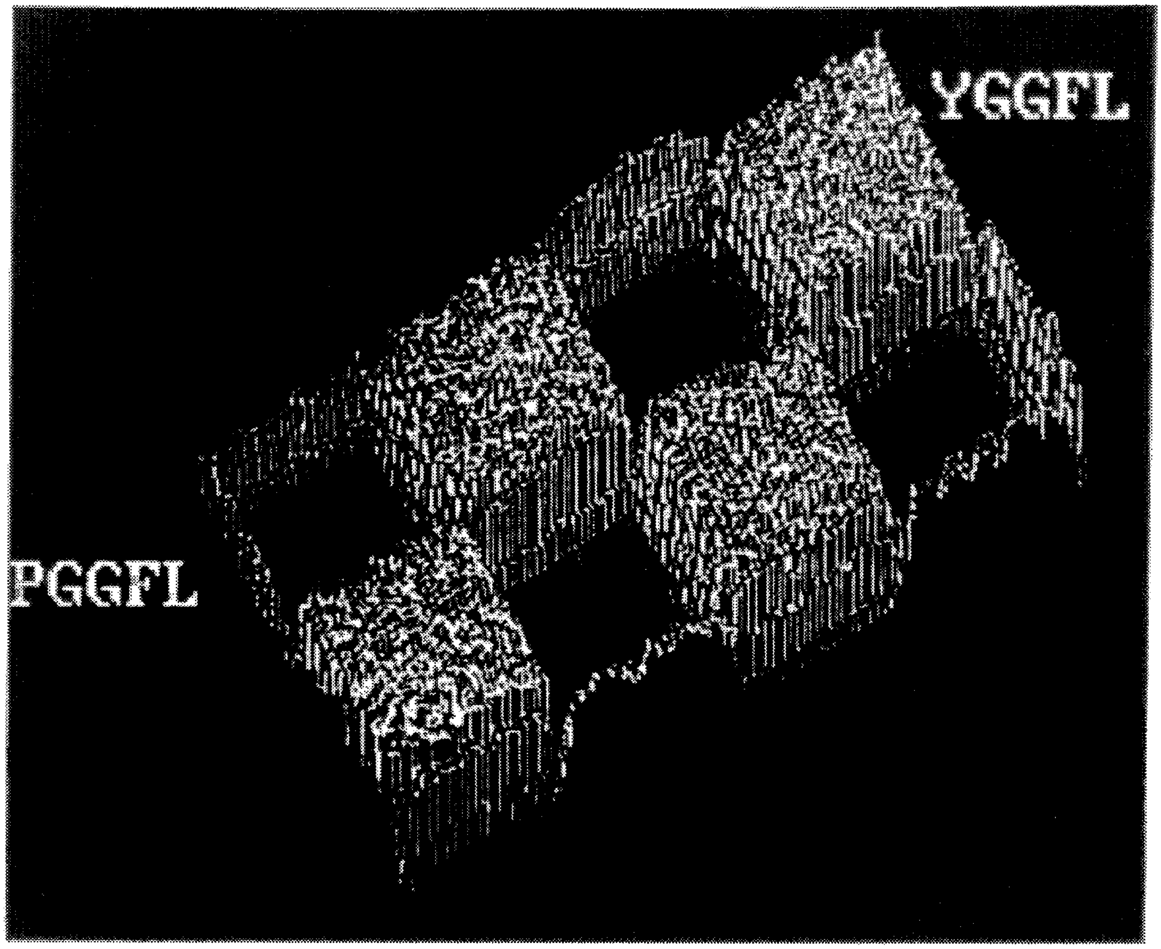
FIG. 3 is a three-dimensional representation of a portion of the checkerboard array of YGGFL and PGGFL.

A three-dimensional representation of the fluorescence intensity data in a portion of the checkboard is shown in FIG. 3. This figure shows that the border between synthesis sites is sharp. The height of each spike in this display is linearly proportional to the integrated fluorescence intensity in a 2.5 μm pixel. The transition between PGGFL and YGGFL occurs within two spikes (5 μm). There is little variation in the fluorescence intensity of different YGGFL squares. The mean intensity of sixteen YGGFL synthesis sites was $2.03\times10^5$ counts and the standard deviation was $9.6\times10^3$ counts.

III. Synthesis

A. Reactor System

Figure 4:
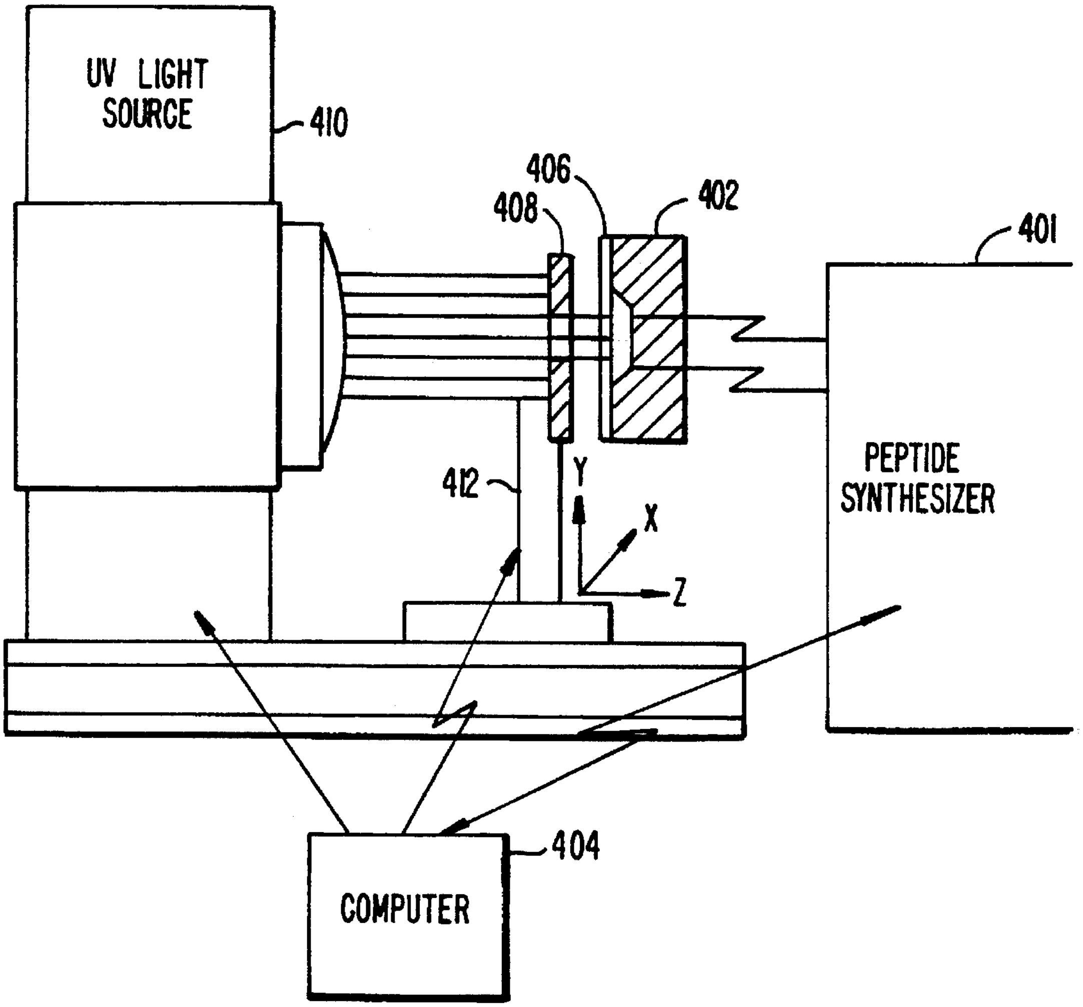
FIG. 4 schematically illustrates an automated system for synthesizing diverse polymer sequences.
Figure 5A:
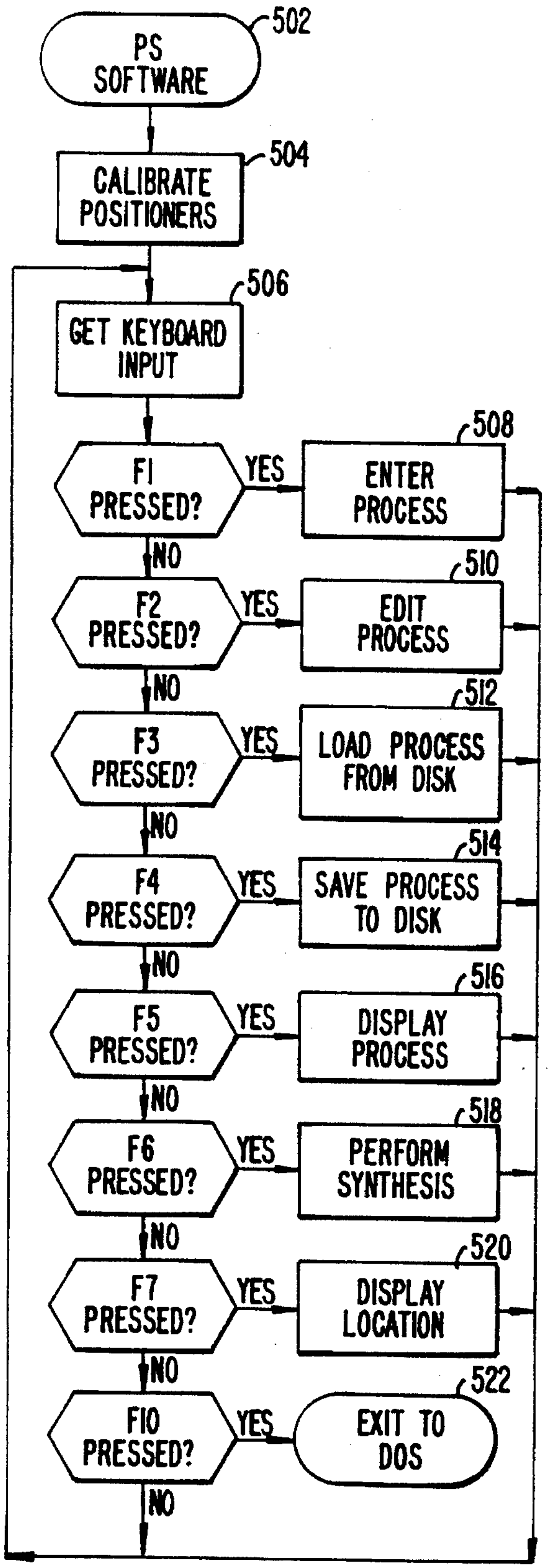
FIG. 5*a* and 5*b* illustrate operation of a program for polymer sythesis.
Figure 5B:
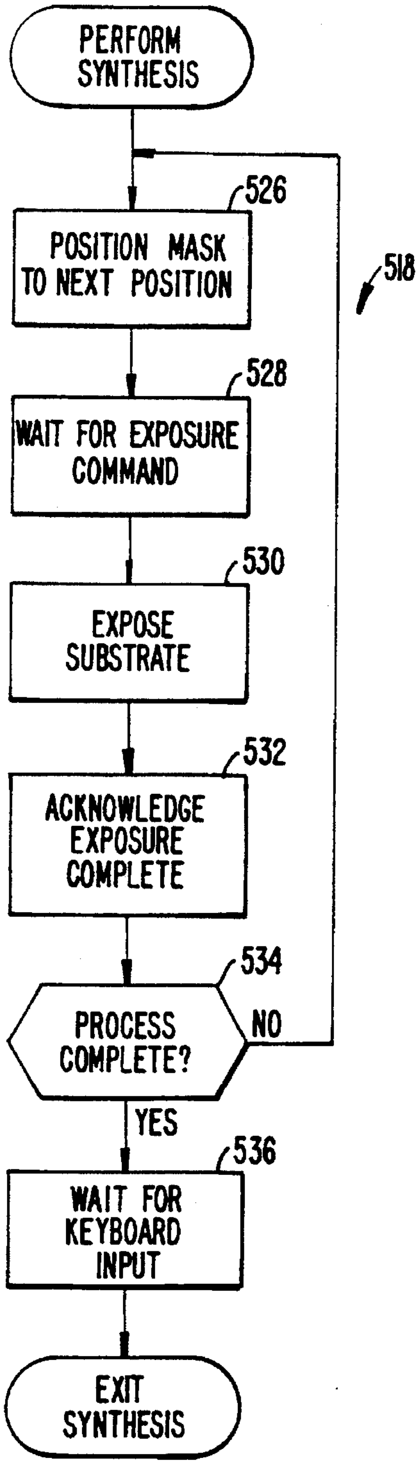

FIG. 4 schematically illustrates a device used to synthesize diverse polymer sequences on a substrate. The device includes an automated peptide synthesizer 401. The automated peptide synthesizer is a device which flows selected reagents through a flow cell 402 under the direction of a computer 404. In a preferred embodiment the synthesizer is an ABI Peptide Synthesizer, model no. 431A. The computer may be selected from a wide variety of computers or discrete logic including for, example, an IBM PC-AT or similar computer linked with appropriate internal control systems in the peptide synthesizer. The PC is provided with signals from the board computer indicative of, for example, the end of a coupling cycle.

Substrate 406 is mounted on the flow cell, forming a cavity between the substrate and the flow cell. Selected reagents flow through this cavity from the peptide synthesizer at selected times, forming an array of peptides on the face of the substrate in the cavity. Mounted above the substrate, and preferably in contact with the substrate is a mask 408. Mask 408 is transparent in selected regions to a selected wavelength of light and is opaque in other regions to the selected wavelength of light. The mask is illuminated with a light source 410 such as a UV light source. In one specific embodiment the light source 410 is a model no. 82420 made by Oriel. The mask is held and translated by an x-y-z translation stage 412 such as an x-y translation stage made by Newport Corp. The computer coordinates action of the peptide synthesizer, x-y translation stage, and light source. Of course, the invention may be used in some embodiments with translation of the substrate instead of the mask.

In operation, the substrate is mounted on the reactor cavity. The slide, with its surface protected by a suitable photo removable protective group, is exposed to light at selected locations by positioning the mask and illuminating the light source for a desired period of time (such as, for example, 1 sec to 60 min in the case of peptide synthesis). A selected peptide or other monomer/polymer is pumped through the reactor cavity by the peptide synthesizer for binding at the selected locations on the substrate. After a selected reaction time (such as about 1 sec to 300 min in the case of peptide reactions) the monomer is washed from the system, the mask is appropriately repositioned or replaced, and the cycle is repeated. In most embodiments of the invention, reactions may be conducted at or near ambient temperature.

FIGS. *5a* and *5b* are flow charts of the software used in operation of the reactor system. At step 502 the peptide synthesis software is initialized. At step 504 the system calibrates positioners on the x-y translation stage and begins a main loop. At step 506 the system determines which, if any, of the function keys on the computer have been pressed. If F1 has been pressed, the system prompts the user for input of a desired synthesis process. If the user enters F2, the system allows a user to edit a file for a synthesis process at step 510. If the user enters F3 the system loads a process from a disk at step 512. If the user enters F4 the system saves an entered or edited process to disk at step 514. If the user selects F5 the current process is displayed at step 516 while selection of F6 starts the main portion of the program, i.e., the actual synthesis according to the selected process. If the user selects F7 the system displays the location of the synthesized peptides, while pressing F10 returns the user to the disk operating system.

FIG. *5b* illustrates the synthesis step 518 in greater detail. The main loop of the program is started in which the system first moves the mask to a next position at step 526. During the main loop of the program, necessary chemicals flow through the reaction cell under the direction of the on-board computer in the peptide synthesizer. At step 528 the system then waits for an exposure command and, upon receipt of the exposure command exposes the substrate for a desired time at step 530. When an acknowledge of exposure complete is received at step 532 the system determines if the process is complete at step 534 and, if so, waits for additional keyboard input at step 536 and, thereafter, exits the perform synthesis process.

A computer program used for operation of the system described above is included as microfiche Appendix A (Copyright, 1990, Affymax Technologies N.V., all rights reserved). The program is written in Turbo C++ (Borland Int'l) and has been implemented in an IBM compatible system. The motor control software is adapted from software produced by Newport Corporation. It will be recognized that a large variety of programming languages could be utilized without departing from the scope of the invention herein. Certain calls are made to a graphics program in "Programmer Guide to PC and PS2 Video Systems" (Wilton, Microsoft Press, 1987), which is incorporated herein by reference for all purposes.

Alignment of the mask is achieved by one of two methods in preferred embodiments. In a first embodiment the system relies upon relative alignment of the various components, which is normally acceptable since x-y-z translation stages are capable of sufficient accuracy for the purposes herein. In alternative embodiments, alignment marks on the substrate are coupled to a CCD device for appropriate alignment.

According to some embodiments, pure reagents are not added at each step, or complete photolysis of the protective groups is not provided at each step. According to these embodiments, multiple products will be formed in each synthesis site. For example, if the monomers A and B are mixed during a synthesis step, A and B will bind to deprotected regions, roughly in proportion to their concentration in solution. Hence, a mixture of compounds will be formed in a synthesis region. A substrate formed with mixtures of compounds in various synthesis regions may be used to perform, for example, an initial screening of a large number of compounds, after which a smaller number of compounds in regions which exhibit high binding affinity are further screened. Similar results may be obtained by only partially photolyzing a region, adding a first monomer, re-photolyzing the same region, and exposing the region to a second monomer.

B. Binary Synthesis Strategy

In a light-directed chemical synthesis, the products formed depend on the pattern and order of masks, and on the order of reactants. To make a set of products there will in general be "n" possible masking schemes. In preferred embodiments of the invention herein a binary synthesis strategy is utilized. The binary synthesis strategy is illustrated herein primarily with regard to a masking strategy, although it will be applicable to other polymer synthesis strategies such as the pin strategy, and the like.

In a binary synthesis strategy, the substrate is irradiated with a first mask, exposed to a first building block, irradiated with a second mask, exposed to a second building block, etc. Each.combination of masked irradiation and exposure to a building block is referred to herein as a "cycle."

In a preferred binary masking scheme, the masks for each cycle allow irradiation of half of a region of interest on the substrate and protection of the remaining half of the region of interest. By "half" it is intended herein not to mean exactly one-half the region of interest, but instead a large fraction of the region of interest such as from about 30 to 70 percent of the region of interest. It will be understood that the entire masking scheme need not take a binary form; instead non-binary cycles may be introduced as desired between binary cycles.

In preferred embodiments of the binary masking scheme, a given cycle illuminates only about half of the region which was illuminated in a previous cycle, while protecting the remaining half of the illuminated portion from the previous cycle. Conversely, in such preferred embodiments, a given cycle illuminates half of the region which was protected in the previous cycle and protects half the region which was protected in a previous cycle.

The synthesis strategy is most readily illustrated and handled in matrix notation. At each synthesis site, the determination of whether to add a given monomer is a binary process. Therefore, each product element $P_j$ is given by the dot product of two vectors, a chemical reactant vector, e.g., C=[A,B,C,D], and a binary vector $\sigma_j$. Inspection of the products in the example below for a four-step synthesis, shows that in one four-step synthesis $\sigma_1$=[1,0,1,0], $\sigma_2$=[1, 0,0,1], $\sigma_3$=[0,1,1,0], and $\sigma_4$=[0,1,0,1], where a 1 indicates illumination and a 0 indicates protection. Therefore, it becomes possible to build a "switch matrix" S from the column vectors $\sigma_j$ (j=1,k where k is the number of products).

$$\begin{array}{ccccc} & \sigma_1 & \sigma_2 & \sigma_3 & \sigma_4 \\ S = & 1 & 1 & 0 & 0 \\ & 0 & 0 & 1 & 1 \\ & 1 & 0 & 1 & 0 \\ & 0 & 1 & 0 & 1 \end{array}$$

The outcome P of a synthesis is simply P=CS, the product of the chemical reactant matrix and the switch matrix.

The switch matrix for an n-cycle synthesis yielding k products has n rows and k columns. An important attribute of S is that each row specifies a mask. A two-dimensional mask $m_j$ for the jth chemical step of a synthesis is obtained directly from the jth row of S by placing the elements $s_{j1}$, . . . $s_{jk}$ into, for example, a square format. The particular arrangement below provides a square format, although linear or other arrangements may be utilized.

$$S = \begin{array}{cccc} s_{11} & s_{12} & s_{13} & s_{14} \\ s_{21} & s_{22} & s_{23} & s_{24} \\ s_{31} & s_{32} & s_{33} & s_{34} \\ s_{41} & s_{42} & s_{43} & s_{44} \end{array} \qquad m_j = \begin{array}{cc} s_{j1} & s_{j2} \\ s_{j3} & s_{j4} \end{array}$$

Of course, compounds formed in a light-activated synthesis can be positioned in any defined geometric array. A square or rectangular matrix is convenient but not required. The rows of the switch matrix may be transformed into any convenient array as long as equivalent transformations are used for each row.

For example, the masks in the four-step synthesis below are then denoted by:

$$m_1 = \begin{array}{cc} 1 & 1 \\ 0 & 0 \end{array} \quad m_2 = \begin{array}{cc} 0 & 0 \\ 1 & 1 \end{array} \quad m_3 = \begin{array}{cc} 1 & 0 \\ 1 & 0 \end{array} \quad m_4 = \begin{array}{cc} 0 & 1 \\ 0 & 1 \end{array}$$

where 1 denotes illumination (activation) and 0 denotes no illumination.

The matrix representation is used to generate a desired set of products and product maps in preferred embodiments. Each compound is defined by the product of the chemical vector and a particular switch vector. Therefore, for each synthesis address, one simply saves the switch vector, assembles all of them into a switch matrix, and extracts each of the rows to form the masks.

In some cases, particular product distributions or a maximal number of products are desired. For example, for C=[A,B,C,D], any switch vector ($\sigma_j$) consists of four bits. Sixteen four-bit vectors exist. Hence, a maximum of 16 different products can be made by sequential addition of the reagents [A,B,C,D]. These 16 column vectors can be assembled in 16! different ways to form a switch matrix. The order of the column vectors defines the masking patterns, and-therefore, the spatial ordering of products but not their makeup. One ordering of these columns gives the following switch matrix (in which "null" (∅) additions are included in brackets for the sake of completeness, although such null additions are elsewhere ignored herein):

$$\begin{array}{cccccccccccccccccccc} & & \sigma 1 & & & & & & & & & & & & & & & \sigma_{16} & \\ & & 1 & 1 & 1 & 1 & 1 & 1 & 1 & 1 & 0 & 0 & 0 & 0 & 0 & 0 & 0 & 0 & A \\ & & [0 & 0 & 0 & 0 & 0 & 0 & 0 & 0 & 1 & 1 & 1 & 1 & 1 & 1 & 1 & 1] & \emptyset \\ S & = & 1 & 1 & 1 & 1 & 0 & 0 & 0 & 0 & 1 & 1 & 1 & 1 & 0 & 0 & 0 & 0 & B \\ & & [0 & 0 & 0 & 0 & 1 & 1 & 1 & 1 & 0 & 0 & 0 & 0 & 1 & 1 & 1 & 1] & \emptyset \\ & & 1 & 1 & 0 & 0 & 1 & 1 & 0 & 0 & 1 & 1 & 0 & 0 & 1 & 1 & 0 & 0 & C \\ & & [0 & 0 & 1 & 1 & 0 & 0 & 1 & 1 & 0 & 0 & 1 & 1 & 0 & 0 & 1 & 1] & \emptyset \\ & & 1 & 0 & 1 & 0 & 1 & 0 & 1 & 0 & 1 & 0 & 1 & 0 & 1 & 0 & 1 & 0 & D \\ & & [0 & 1 & 0 & 1 & 0 & 1 & 0 & 1 & 0 & 1 & 0 & 1 & 0 & 1 & 0 & 1] & \emptyset \end{array}$$

The columns of S according to this aspect of the invention are the binary representations of the numbers 15 to 0. The sixteen products of this binary synthesis are ABCD, ABC, ABD, AB, ACD, AC, AD, A, BCD, BC, BD, B, CD, C, D, and ∅ (null). Also note that each of the switch vectors from the four-step synthesis masks above (and hence the synthesis products) are present in the four bit binary switch matrix. (See columns 6, 7, 10, and 11)

This synthesis procedure provides an easy way for mapping the completed products. The products in the various locations on the substrate are simply defined by the columns of the switch matrix (the first column indicating, for example, that the product ABCD will be present in the upper left-hand location of the substrate). Furthermore, if only selected desired products are to be made, the mask sequence can be derived by extracting the columns with the desired sequences. For example, to form the product set ABCD, ABD, ACD, AD, BCD, BD, CD, and D, the masks are formed by use of a switch matrix with only the 1st, 3rd, 5th, 7th, 9th, 11th, 13th, and 15th columns arranged into the switch matrix:

$$S = \begin{matrix} 1 & 1 & 1 & 1 & 0 & 0 & 0 & 0 \\ 1 & 1 & 0 & 0 & 1 & 1 & 0 & 0 \\ 1 & 0 & 1 & 0 & 1 & 0 & 1 & 0 \\ 1 & 1 & 1 & 1 & 1 & 1 & 1 & 1 \end{matrix}$$

To form all of the polymers of length 4, the reactant matrix [ABCDABCDABCDABCD] is used. The switch matrix will be formed from a matrix of the binary numbers from 0 to $2^{16}$ arranged in columns. The columns having four monomers are than selected and arranged into a switch matrix. Therefore, it is seen that the binary switch matrix in general will provide a representation of all the products which can be made from an n-step synthesis, from which the desired products are then extracted.

The rows of the binary switch matrix will, in preferred embodiments, have the property that each masking step illuminates half of the synthesis area. Each masking step also factors the preceding masking step; that is, half of the region that was illuminated in the preceding step is again illuminated, whereas the other half is not. Half of the region that was unilluminated in the preceding step is also illuminated, whereas the other half is not. Thus, masking is recursive. The masks are constructed, as described previously, by extracting the elements of each row and placing them in a square array. For example, the four masks in S for a four-step synthesis are:

$$m_1 = \begin{matrix} 1 & 1 & 1 & 1 \\ 1 & 1 & 1 & 1 \\ 0 & 0 & 0 & 0 \\ 0 & 0 & 0 & 0 \end{matrix} \quad m_2 = \begin{matrix} 1 & 1 & 1 & 1 \\ 0 & 0 & 0 & 0 \\ 1 & 1 & 1 & 1 \\ 0 & 0 & 0 & 0 \end{matrix}$$

$$m_3 = \begin{matrix} 1 & 1 & 0 & 0 \\ 1 & 1 & 0 & 0 \\ 1 & 1 & 0 & 0 \\ 1 & 1 & 0 & 0 \end{matrix} \quad m_4 = \begin{matrix} 1 & 0 & 1 & 0 \\ 1 & 0 & 1 & 0 \\ 1 & 0 & 1 & 0 \\ 1 & 0 & 1 & 0 \end{matrix}$$

The recursive factoring of masks allows the products of a light-directed synthesis to be represented by a polynomial. (Some light activated syntheses can only be denoted by irreducible, i.e., prime polynomials.) For example, the polynomial corresponding to the top synthesis of FIG. 9*a* (discussed below) is $$P=(A+B)(C+D)$$

A reaction polynomial may be expanded as though it were an algebraic expression, provided that the order of joining of reactants $X_1$ and $X_2$ is preserved ($X_1X_2 \neq X_2X_1$), i.e., the products are not commutative. The product then is AC+AD+BC+BD. The polynomial explicitly specifies the reactants and implicitly specifies the mask for each step. Each.pair of parentheses demarcates a round of synthesis. The chemical reactants of a round (e.g., A and B) react at nonoverlapping sites and hence cannot combine with one other. The synthesis area is divided equally amongst the elements of a round (e.g., A is directed to one-half of the area and B to the other half). Hence, the masks for a round (e.g., the masks $m_A$ and $m_B$) are orthogonal and form an orthonormal set. The polynomial notation also signifies that each element in a round is to be joined to each element of the next round (e.g., A with C, A with D, B with C, and B with D). This is accomplished by having $m_c$ overlap $m_A$ an $m_B$ equally, and likewise for $m_D$. Because C and D are elements of a round, $m_c$ and $m_D$ are orthogonal to each other and form an orthonormal set.

The polynomial representation of the binary synthesis described above, in which 16 products are made from 4 reactants, is $$P=(A+\emptyset)(B+\emptyset)(C+\emptyset)(D+\emptyset)$$

which gives ABCD, ABC, ABD, AB, ACD, AC, AD, A, BCD, BC, BD, B, CD, C, D, and 0 when expanded (with the rule that $\emptyset X=X$ and $X\emptyset=X$, and remembering that joining is ordered). In a binary synthesis, each round contains one reactant and one null (denoted by $\emptyset$). Half of the synthesis area receives the reactant and the other half receives nothing. Each mask overlaps every other mask equally.

Binary rounds and non-binary rounds can be interspersed as desired, as in $P=(A+\emptyset)(B)(C+D+\emptyset)(E+F+G)$ The 18 compounds formed are ABCE, ABCF, ABCG, ABDE, ABDF, ABDG, ABE, ABF, ABG, BCE, BCF, BCG, BDE, BDF, BDG, BE, BF, and BG. The switch matrix S for this 7-step synthesis is $$S = \begin{matrix} 1 & 1 & 1 & 1 & 1 & 1 & 1 & 1 & 1 & 0 & 0 & 0 & 0 & 0 & 0 & 0 & 0 & 0 \\ 1 & 1 & 1 & 1 & 1 & 1 & 1 & 1 & 1 & 1 & 1 & 1 & 1 & 1 & 1 & 1 & 1 & 1 \\ 1 & 1 & 1 & 0 & 0 & 0 & 0 & 0 & 0 & 1 & 1 & 1 & 0 & 0 & 0 & 0 & 0 & 0 \\ 0 & 0 & 0 & 1 & 1 & 1 & 0 & 0 & 0 & 0 & 0 & 0 & 1 & 1 & 1 & 0 & 0 & 0 \\ 1 & 0 & 0 & 1 & 0 & 0 & 1 & 0 & 0 & 1 & 0 & 0 & 1 & 0 & 0 & 1 & 0 & 0 \\ 0 & 1 & 0 & 0 & 1 & 0 & 0 & 1 & 0 & 0 & 1 & 0 & 0 & 1 & 0 & 0 & 1 & 0 \\ 0 & 0 & 1 & 0 & 0 & 1 & 0 & 0 & 1 & 0 & 0 & 1 & 0 & 0 & 1 & 0 & 0 & 1 \end{matrix}$$

The round denoted by (B) places B in all products because the reaction area was uniformly activated (the mask for B consisted entirely of 1's).

The number of compounds k formed in a synthesis consisting of r rounds, in which the ith round has $b_i$ chemical reactants and $z_i$ nulls, is $$k=\Sigma(b_i+z_i)$$

and the number of chemical steps n is $$n=\Sigma b_i$$

The number of compounds synthesized when b=a and z=0 in all rounds is $a^{n/a}$, compared with $2^n$ for a binary synthesis. For n=20 and a=5, 625 compounds (all tetramers) would be formed, compared with $1.049\times10^6$ compounds in a binary synthesis with the same number of chemical steps.

It should also be noted that rounds in a polynomial can be nested, as in $$(A+(B+\emptyset)(C+\emptyset))(D+\emptyset)$$

The products are AD, BCD, BD, CD, D, A, BC, B, C, and $\emptyset$.

Figure 6A:
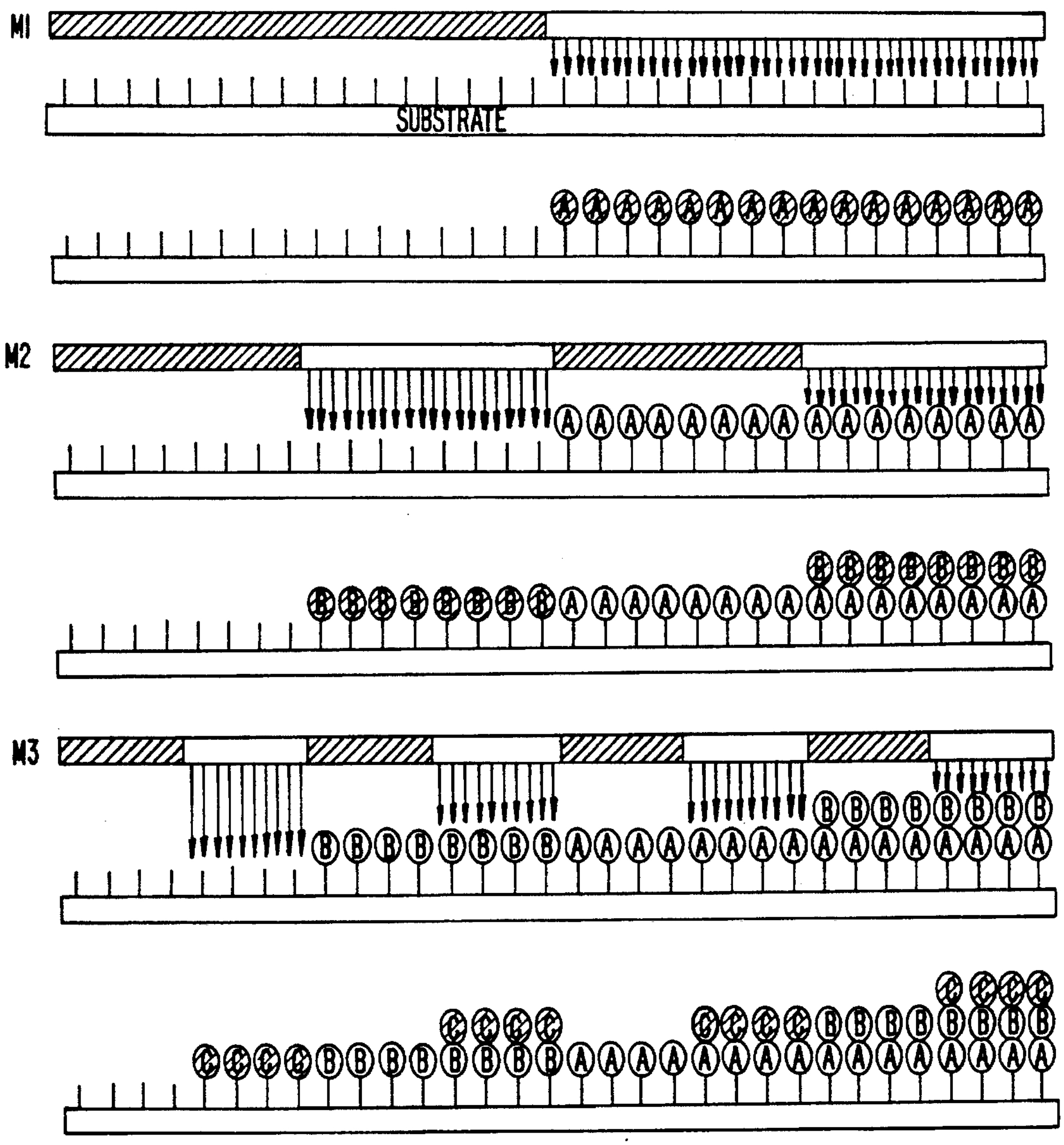
FIG. 6 is a schematic illustration of a "pure" binary masking strategy.
Figure 6:
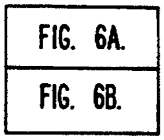
Figure 6B:
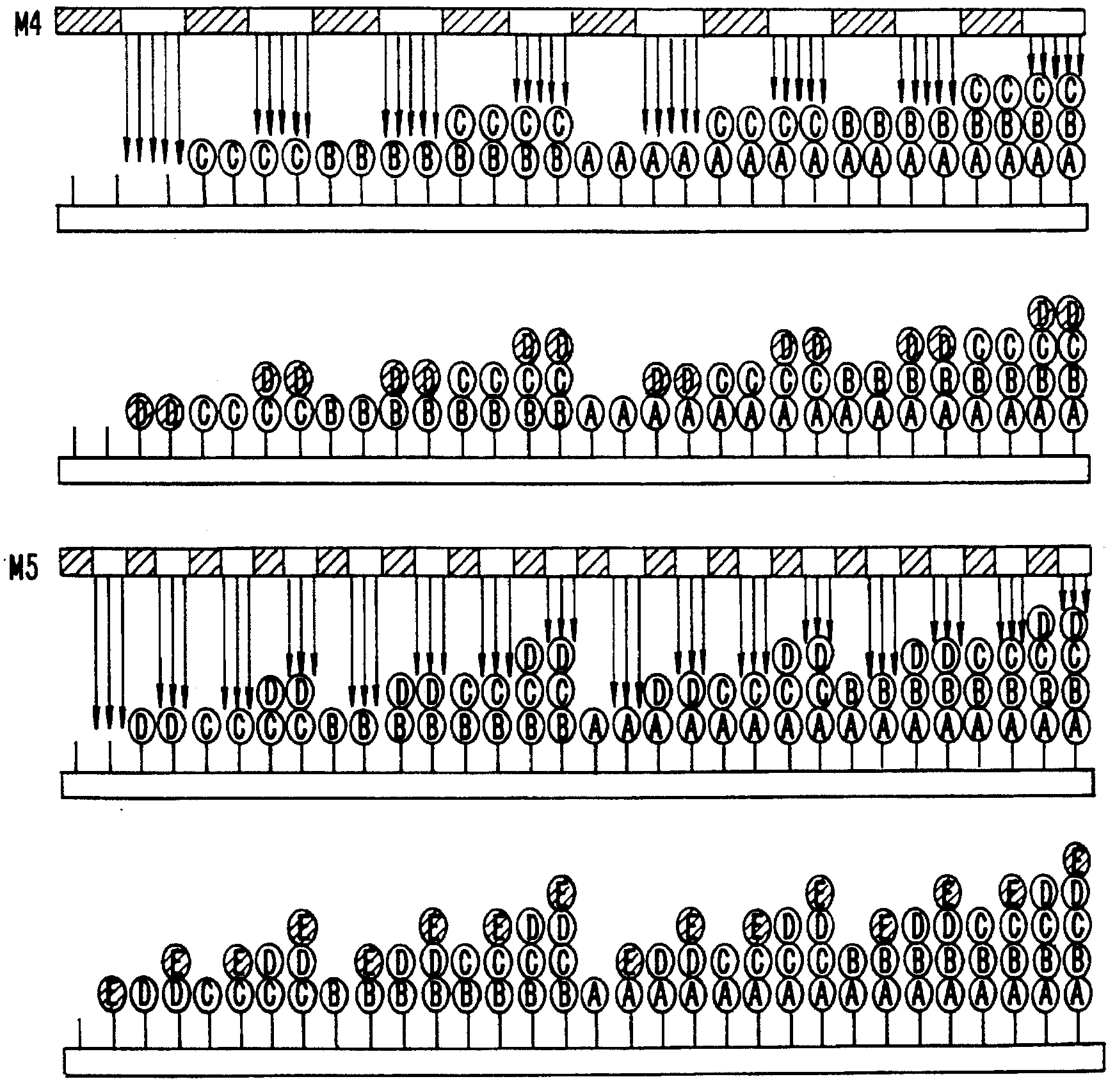

Binary syntheses are attractive for two reasons. First, they generate the maximal number of products ($2^n$) for a given number of chemical steps (n). For four reactants, 16 compounds are formed in the binary synthesis, whereas only 4 are made when each round has two reactants. A 10-step binary synthesis yields 1,024 compounds, and a 20-step synthesis yields 1,048,576. Second, products formed in a binary synthesis are a complete nested set with lengths ranging from 0 to n. All compounds that can be formed by deleting one or more units from the longest product (the n-mer) are present. Contained within the binary set are the smaller sets that would be formed from the same reactants using any other set of masks (e.g., AC, AD, BC, and BD formed in the synthesis shown in FIG. 6 are present in the set of 16 formed by the binary synthesis). In some cases, however, the experimentally achievable spatial resolution may not suffice to accommodate all the compounds formed. Therefore, practical limitations may require one to select a particular subset of the possible switch vectors for a given synthesis.

1. Example

FIG. 6 illustrates a synthesis with binary masking scheme. The binary masking scheme provides the greatest number of sequences for a given number of cycles. According to this embodiment, a mask ml allows illumination of half of the substrate. The substrate is then exposed to the building block A, which binds at the illuminated regions.

Thereafter, the mask m2 allows illumination of half of the previously illuminated region, while protecting half of the previously illuminated region. The building block B is then added, which binds at the illuminated regions from m2.

The process continues with masks m3, m4, and m5, resulting in the product array shown in the bottom portion of the figure. The process generates 32 (2 raised to the power of the number of monomers) sequences with 5 (the number of monomers) cycles.

2. Example

Figure 7A:
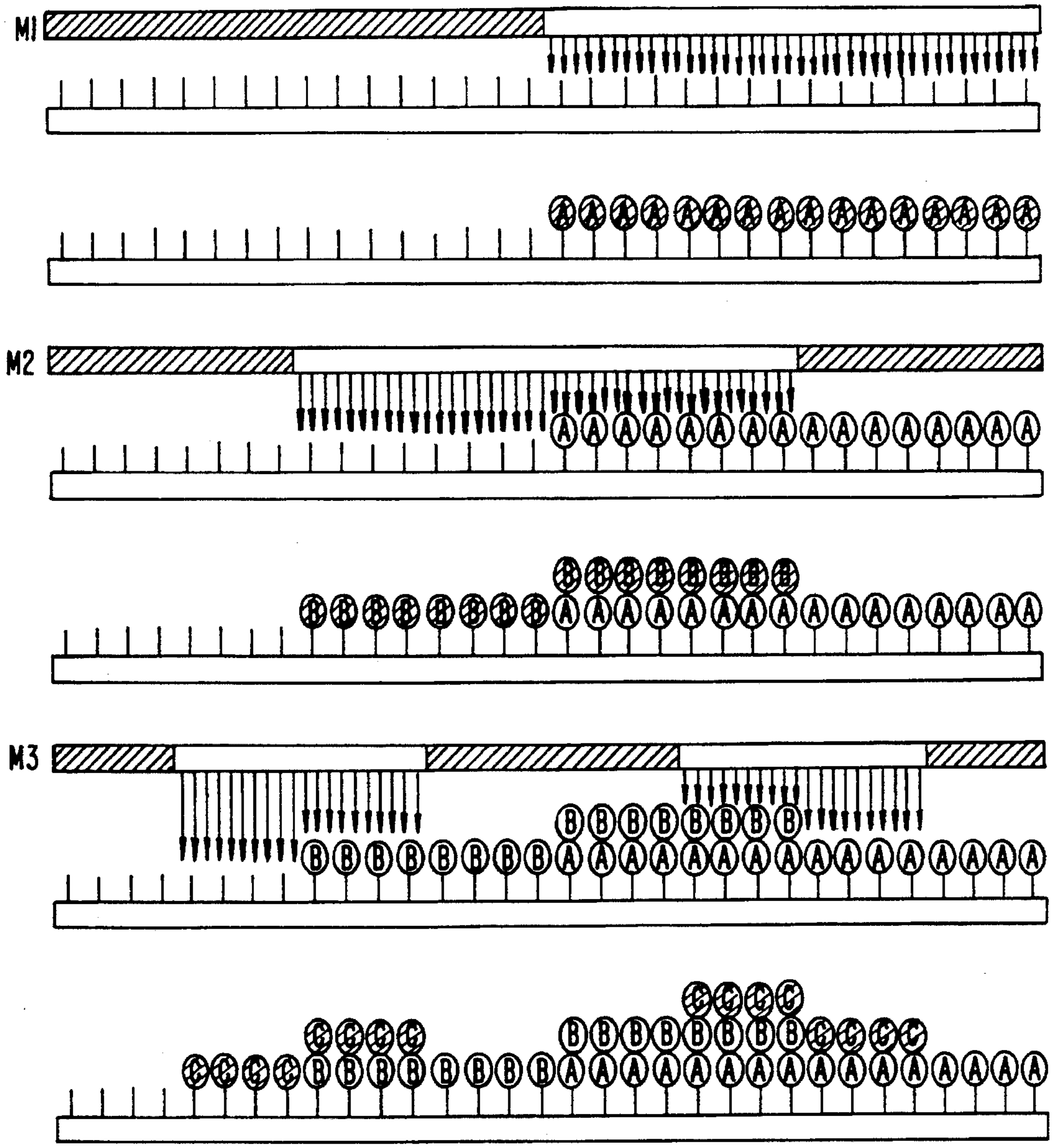
FIG. 7 is a schematic illustration of a gray code binary masking strategy.
Figure 7:
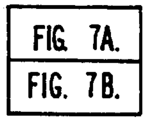
Figure 7B:
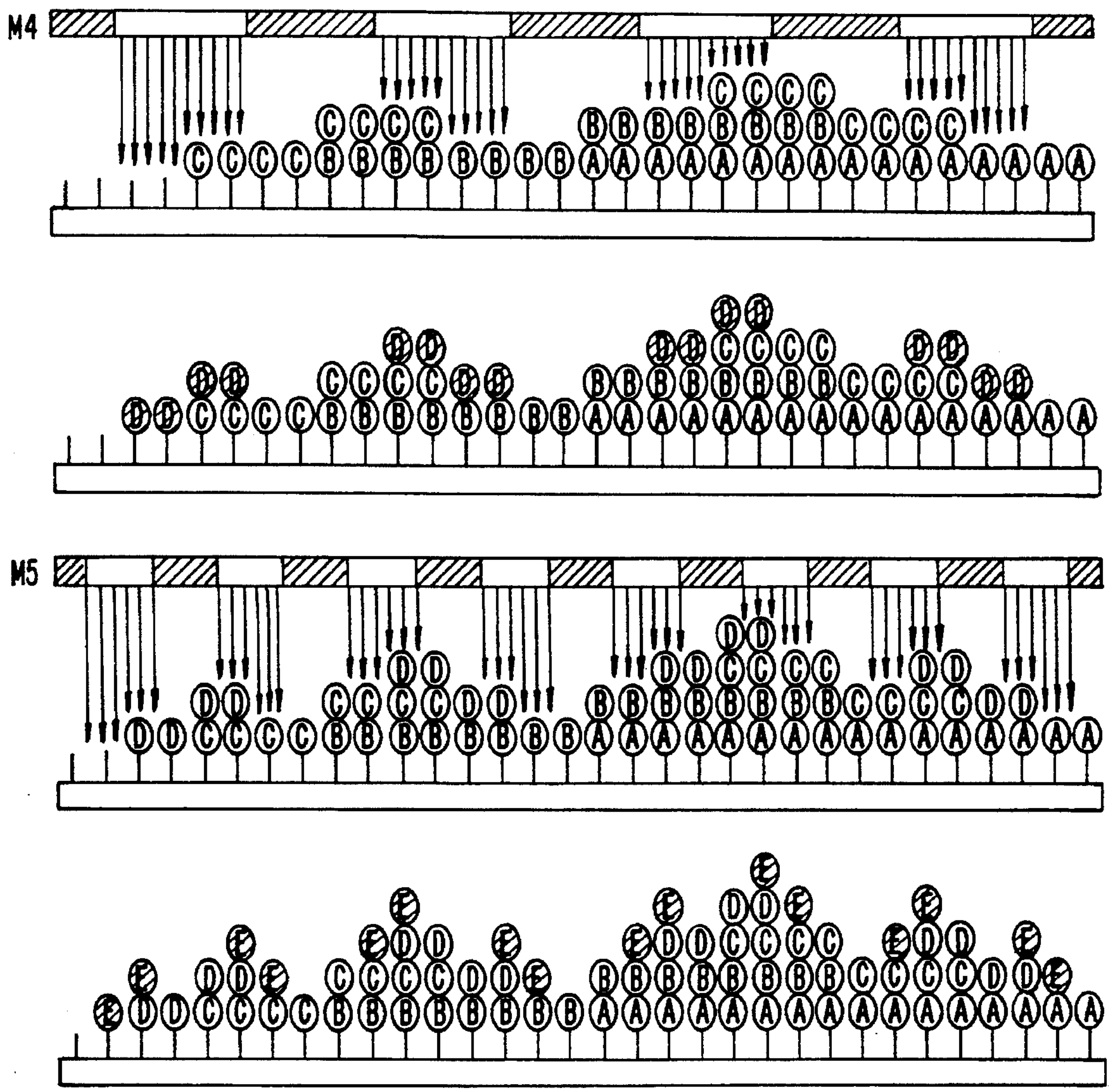

FIG. 7 illustrates another preferred binary masking scheme which is referred to herein as the gray code masking scheme. According to this embodiment, the masks ml to m5 are selected such that a side of any given synthesis region is defined by the edge of only one mask. The site at which the sequence BCDE is formed, for example, has its right edge defined by m5 and its left side formed by mask m4 (and no other mask is aligned on the sides of this site). Accordingly, problems created by misalignment, diffusion of light under the mask and the like will be minimized.

3. Example

Figure 8A:
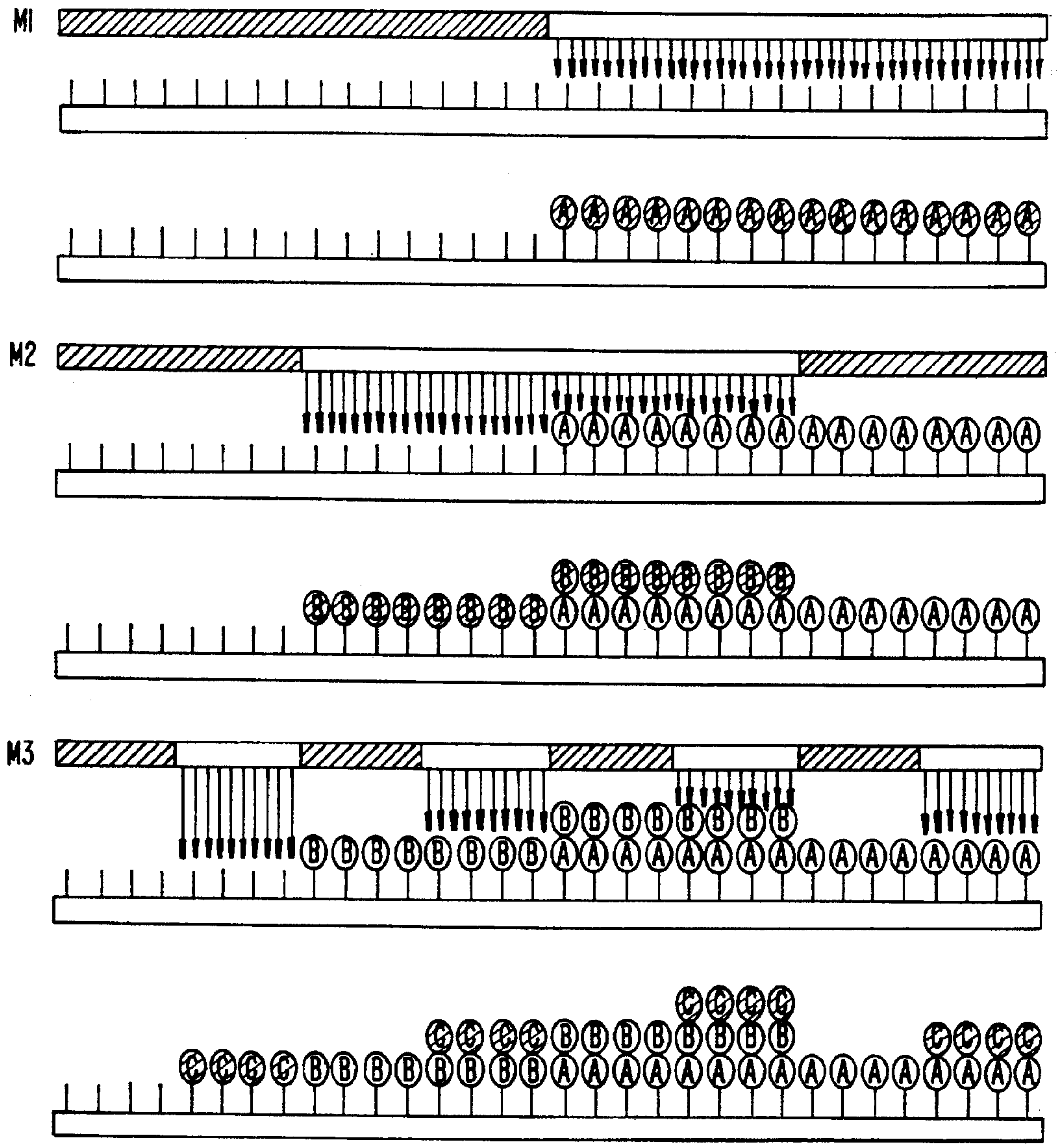
FIG. 8 is a schematic illustration of a modified gray code binary masking strategy.
Figure 8:
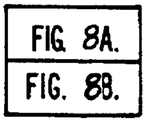
Figure 8B:
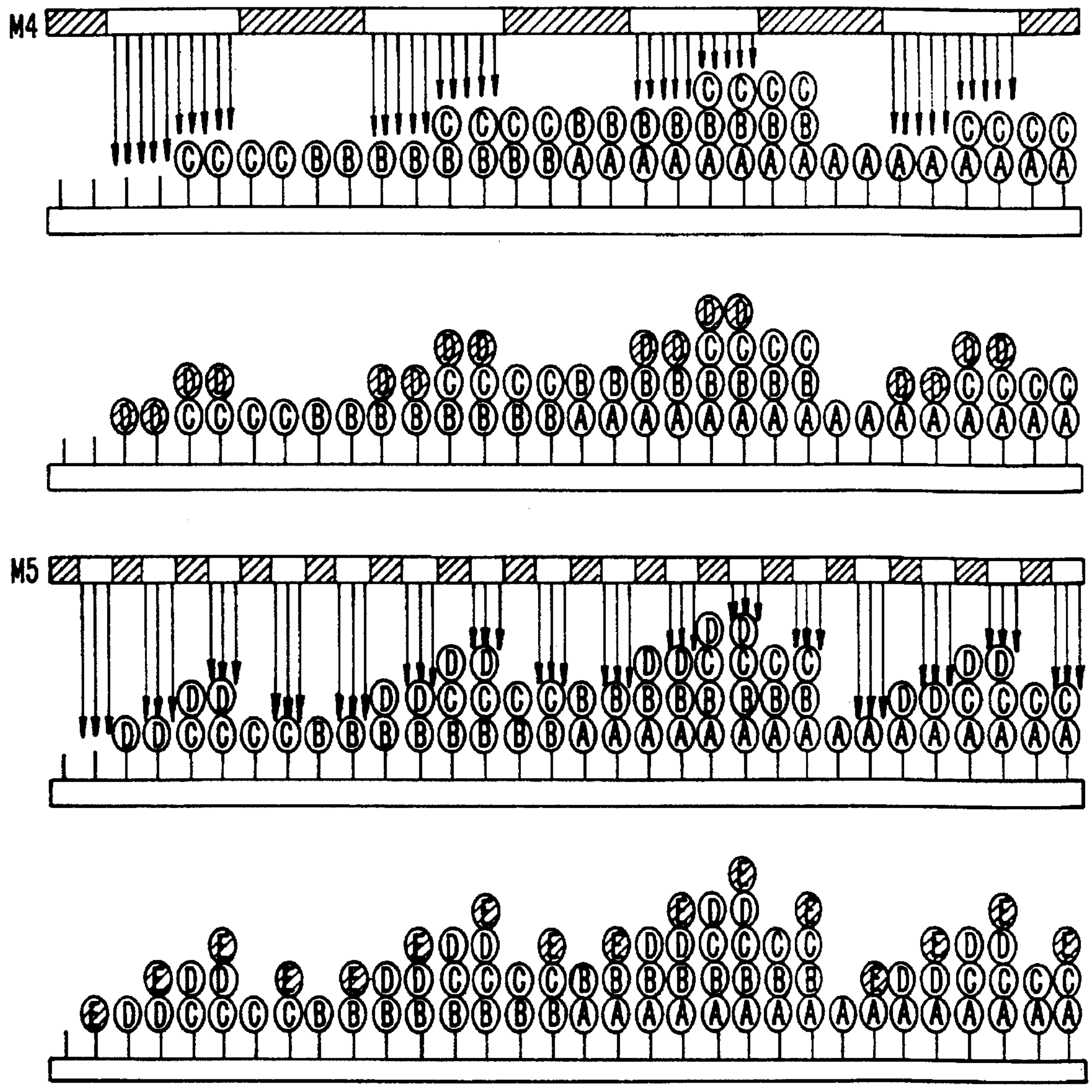

FIG. 8 illustrates another binary masking scheme. According to this scheme, referred to herein as a modified gray code masking scheme, the number of masks needed is minimized. For example, the mask m2 could be the same mask as ml and simply translated laterally. Similarly, the mask m4 could be the same as mask m3 and simply translated laterally.

4. Example

Figure 9A:
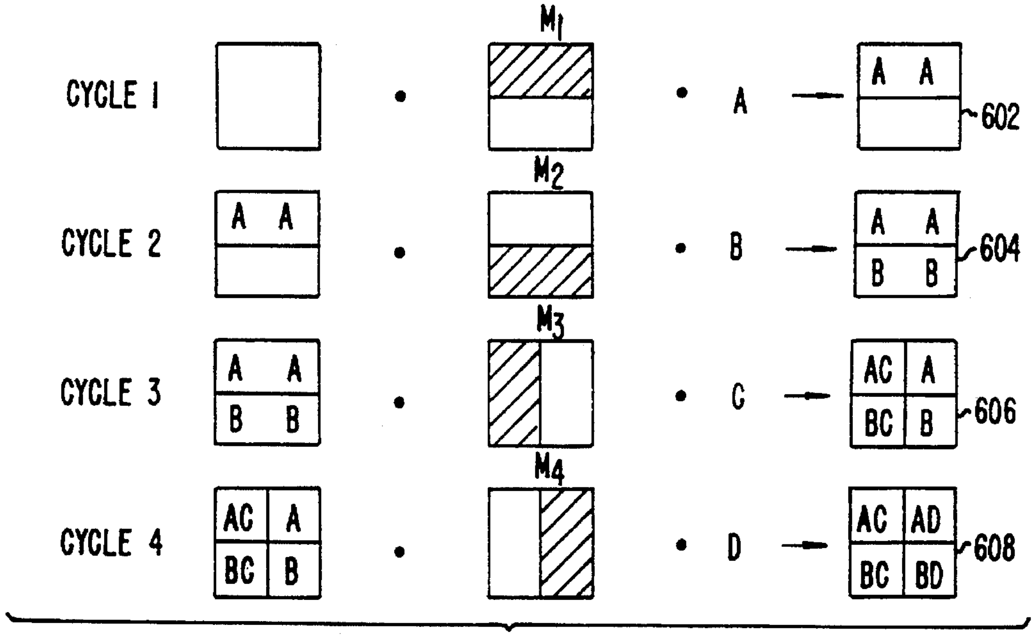
FIG. 9*a* schematically illustrates a masking scheme for a four step synthesis.

A four-step synthesis is shown in FIG. 9*a*. The reactants are the ordered set (A,B,C,D). In the first cycle, illumination through $m_1$ activates the upper half of the synthesis area. Building block A is then added to give the distribution 602. Illumination through mask $m_2$ (which activates the lower half), followed by addition of B yields the next intermediate distribution 604. C is added after illumination through $m_3$ (which activates the left half) giving the distribution 604, and D after illumination through $m_4$ (which activates the right half), to yield the final product pattern 608 (AC,AD, BC,BD).

5. Example

Figure 9B:
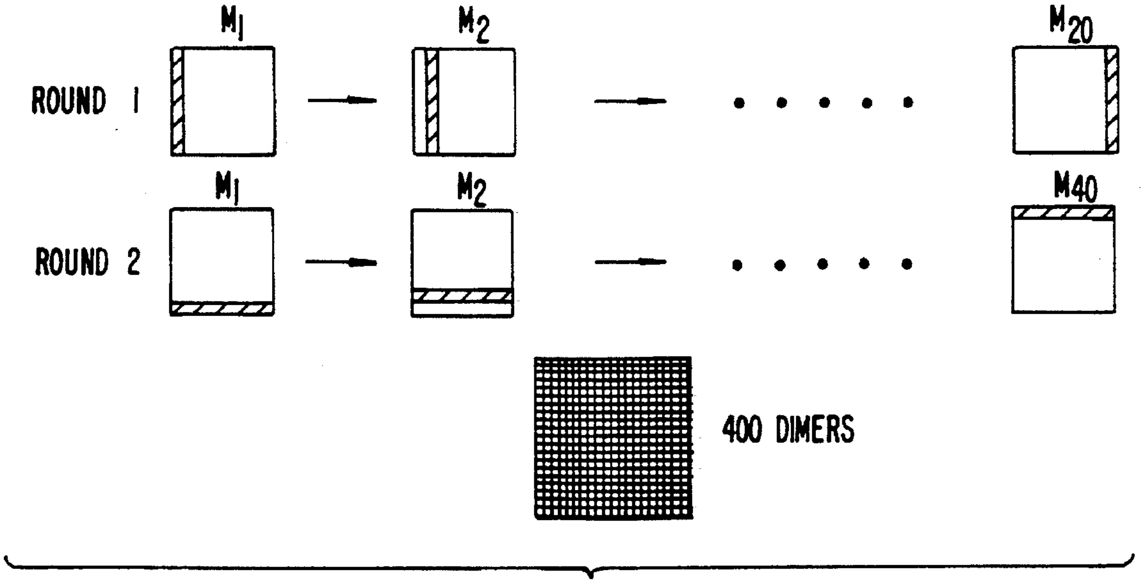
FIG. 9*b* schematically illustrates synthesis of all 400 peptide dimers.

The above masking strategy for the synthesis may be extended for all 400 dipeptides from the 20 naturally occurring amino acids as shown in FIG. 9*b*. The synthesis consists of two rounds,-with 20 photolysis and chemical coupling cycles per round. In the first cycle of round 1, mask 1 activates 1/20th of the substrate for coupling with the first of 20 amino acids. Nineteen subsequent illumination/coupling cycles in round 1 yield a substrate consisting of 20 rectangular stripes each bearing a distinct member of the 20 amino acids. The masks of round 2 are perpendicular to round 1 masks and therefore a single illumination/coupling cycle in round 2 yields 20 dipeptides. The 20 illumination/coupling cycles of round 2 complete the synthesis of the 400 dipeptides.

6. Example

The power of the binary masking strategy can be appreciated by the outcome of a 10-step synthesis that produced 1,024 peptides. The polynomial expression for this 10-step binary synthesis was:

$$(f+\phi)\ (Y+\phi)\ (G+\phi)\ (A+\phi)\ (G+\phi)\ (T+\phi)\ (F+\phi)\ (L+\phi)\ (S+\phi)\ (F+\phi)$$

Each peptide occupied a 400×400 μm square. A 32×32 peptide array (1,024 peptides, including the null peptide and 10 peptides of l=1, and a limited number of duplicates) was clearly evident in a fluorescence scan following side group deprotection and treatment with the antibody 3E7 and fluorescinated antibody. Each synthesis site was a 400×400 μm square.

The scan showed a range of fluorescence intensities, from a background value of 3,300 counts to 22,400 counts in the brightest square (x=20, y=9). Only 15 compounds exhibited an intensity greater than 12,300 counts. The median value of the array was 4,800 counts.

Figure 10:
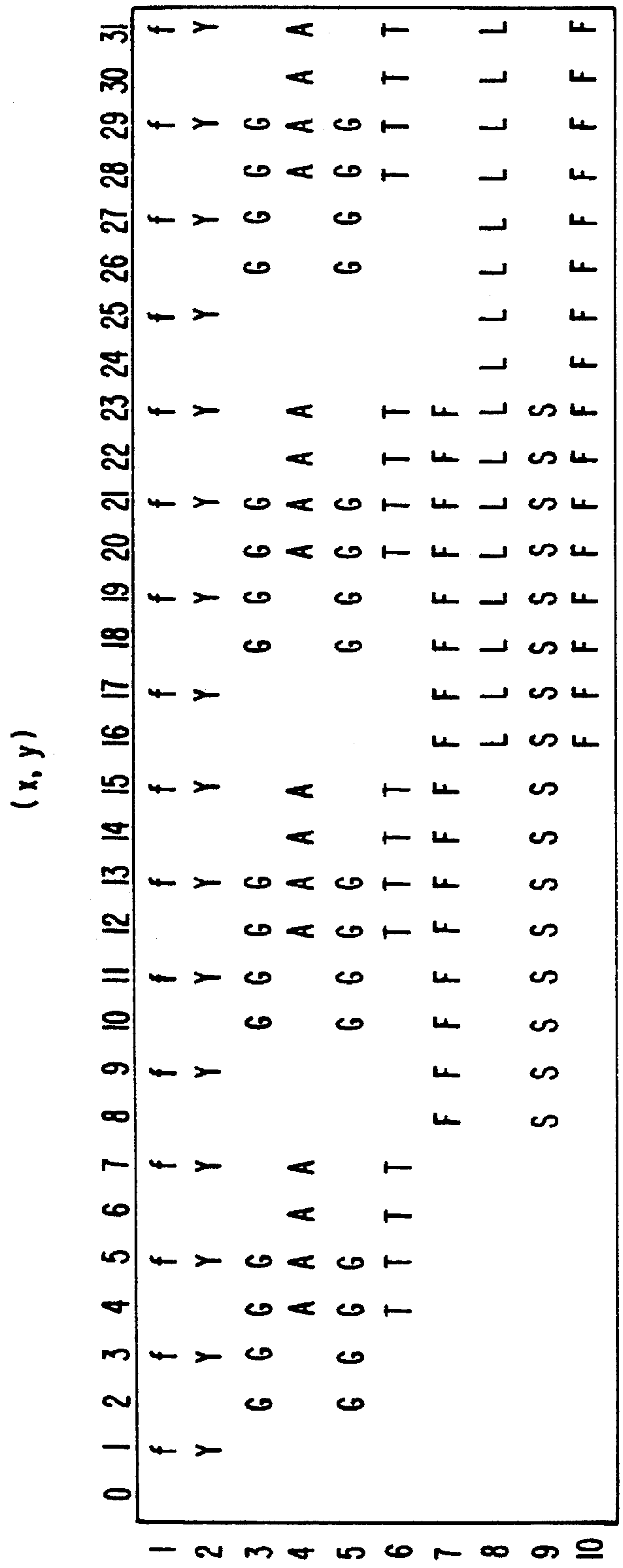
FIG. 10 is a coordinate map for the ten-step binary synthesis.

The identity of each peptide in the array could be determined from its x and y coordinates (each range from 0 to 31) and the map of FIG. 10. The chemical units at positions 2, 5, 6, 9, and 10 are specified by the y coordinate and those at positions 1, 3, 4, 7, 8 by the x coordinate. All but one of the peptides was shorter than 10 residues. For example, the peptide at x=12 and y =3 is YGAGF (SEQ. ID NO: 3) (positions 1, 6, 8, 9, and 10 are nulls). YGAFLS (SEQ. ID NO: 4), the brightest element of the array, is at x=20 and y=9.

It is often desirable to deduce a binding affinity of a given peptide from the measured fluorescence intensity. Conceptually, the simplest case is one in which a single peptide binds to a univalent antibody molecule. The fluorescence scan is carried out after the slide is washed with buffer for a defined time. The order of fluorescence intensities is then a measure primarily of the relative dissociation rates of the antibody-peptide complexes. If the on-rate constants are the same (e.g., if they are diffusion-controlled), the order of fluorescence intensities will correspond to the order of binding affinities. However, the situation is sometimes more complex because a bivalent primary antibody and a bivalent secondary antibody are used. The density of peptides in a synthesis area corresponded to a mean separation of ~7 nm, which would allow multivalent antibody-peptide interactions. Hence, fluorescence intensities obtained according to the method herein will often be a qualitative indicator of binding affinity.

Another important consideration is the fidelity of synthesis. Deletions are produced by incomplete photodeprotection or incomplete coupling. The coupling yield per cycle in these experiments is typically between 85% and 95%. Implementing the switch matrix by masking is imperfect because of light diffraction, internal reflection, and scattering. Consequently, stowaways (chemical units that should not be on board) arise by unintended illumination of regions that should be dark. A binary synthesis array contains many of the controls needed to assess the fidelity of a synthesis. For example, the fluorescence signal from a synthesis area nominally containing a tetrapeptide ABCD could come from a tripeptide deletion impurity such as ACD. Such an artifact would be ruled out by the finding that the fluorescence intensity of the ACD-site is less than that of the ABCD site.

The fifteen most highly labelled peptides in the array obtained with the synthesis of 1,024 peptides described above, were YGAFLS (SEQ. ID NO: 4), YGAFS (SEQ. ID NO: 5), YGAFL (SEQ. ID NO: 6), YGGFLS (SEQ. ID NO: 7), YGAF (SEQ. ID NO: 8), YGALS (SEQ. ID NO: 9), YGGFS (SEQ. ID NO: 10), YGAL (SEQ. ID NO: 11), YGAFLF (SEQ. ID NO: 12), YGAF (SEQ. ID NO: 13), YGAFF (SEQ. ID NO: 14), YGGFL (SEQ. ID NO: 15), YGAFSF (SEQ. ID NO: 16) and YGAFLSF (SEQ. ID NO: 17). A striking feature is that all fifteen begin with YG, which agrees with previous work showing that an amino-terminal tyrosine is a key determinant of binding. Residue 3 of this set is either A or G, and residue 4 is either F or L. The exclusion of S and T from these positions is clear cut. The finding that the preferred sequence is YG (A/G) (F/L) fits nicely with the outcome of a study in which a very large library of peptides on phage generated by recombinant DNA methods was screened for binding to antibody 3E7 (see Cwirla et al., *Proc. Natl. Acad. Sci. USA*, (1990) 87:6378, incorporated herein by reference). Additional binary syntheses based on leads from peptides on phage experiments show that YGAFMQ (SEQ. ID NO: 18), YGAFM (SEQ. ID NO: 19), and YGAFQ (SEQ. ID NO: 20) give stronger fluorescence signals than does YGGFM, the immunogen used to obtain antibody 3E7.

Variations on the above masking strategy will be valuable in certain circumstances. For example, if a "kernel" sequence of interest consists of PQR separated from XYZ and the aim is to synthesize peptides in which these units are separated by a variable number of different residues, the kernel can be placed in each peptide by using a mask that has 1's everywhere. The polynomial representation of a suitable synthesis is:

$$(P)\ (Q)\ (R)\ (A+\phi)\ (B+\phi)\ (C+\phi)\ (D+\phi)\ (X)\ (Y)\ (Z)$$

Sixteen peptides will be formed, ranging in length from the 6-mer PQRXYZ to the 10-mer PQRABCDXYZ.

Several other masking strategies will also find value in selected circumstances. By using a particular mask more than once, two or more reactants will appear in the same set of products. For example, suppose that the mask for an 8-step synthesis is

| | |
|---|---|
| A | 11110000 |
| B | 00001111 |
| C | 11001100 |
| D | 00110011 |
| E | 10101010 |
| F | 01010101 |
| G | 11110000 |
| H | 00001111 |

The products are ACEG, ACFG, ADEG, ADFG, BCEH, BCFH, BDEH, and BDFH. A and G always appear together because their additions were directed by the same mask, and likewise for B and H.

C. Linker Selection

According to preferred embodiments the linker molecules used as an intermediary between the synthesized polymers and the substrate are selected for optimum length and/or type for improved binding interaction with a receptor. According to this aspect of the invention diverse linkers of varying length and/or type are synthesized for subsequent attachment of a ligand. Through variations in the length and type of linker, it becomes possible to optimize the binding interaction between an immobilized ligand and its receptor.

The degree of binding between a ligand (peptide, inhibitor, hapten, drug, etc.) and its receptor (enzyme, antibody, etc.) when one of the partners is immobilized on to a substrate will in some embodiments depend on the accessibility of the receptor in solution to the immobilized ligand. The accessibility in turn will depend on the length and/or type of linker molecule employed to immobilize one of the partners. Preferred embodiments of the invention therefore employ the VLSIPS™ technology described herein to generate an array of, preferably, inactive or inert linkers of varying length and/or type, using photochemical protecting groups to selectively expose different regions of the substrate and to build upon chemically-active groups.

In the simplest embodiment of this concept, the same unit is attached to the substrate in varying multiples or lengths in known locations on the substrate via VLSIPS™ techniques to generate an array of polymers of varying length. A.single ligand (peptide, drug, hapten, etc.) is attached to each of them, and an assay is performed with the binding site to evaluate the degree of binding with a receptor that is known to bind to the ligand. In cases where the linker length impacts the ability of the receptor to bind to the ligand, varying levels of binding will be observed. In general, the linker which provides the highest binding will then be used to assay other ligands synthesized in accordance with the techniques herein.

According to other embodiments the binding between a single ligand/receptor pair is evaluated for linkers of diverse monomer sequence. According to these embodiments, the linkers are synthesized in an array in accordance with the techniques herein and have different monomer sequence (and, optionally, different lengths). Thereafter, all of the linker molecules are provided with a ligand known to have at least some binding affinity for a given receptor. The given receptor is then exposed to the ligand and binding affinity is deduced. Linker molecules which provide adequate binding between the ligand and receptor are then utilized in screening studies.

D. Protecting Groups

As discussed above, selectively removable protecting groups allow creation of well defined areas of substrate surface having differing reactivities. Preferably, the protecting groups are selectively removed from the surface by applying a specific activator, such as electromagnetic radiation of a specific wavelength and intensity. More preferably, the specific activator exposes selected areas of surface to remove the protecting groups in the exposed areas.

Protecting groups of the present invention are used in conjunction with solid phase oligomer syntheses, such as peptide syntheses using natural or unnatural amino acids, nucleotide syntheses using deoxyribonucleic and ribonucleic acids, oligosaccharide syntheses, and the like. In addition to protecting the substrate surface from unwanted reaction, the protecting groups block a reactive end of the monomer to prevent self-polymerization. For instance, attachment of a protecting group to the amino terminus of an activated amino acid, such as an N-hydroxysuccinimide-activated ester of the amino acid, prevents the amino terminus of one monomer from reacting with the activated ester portion of another during peptide synthesis. Alternatively, the protecting group may be attached to the carboxyl group of an amino acid to prevent reaction at this site. Most protecting groups can be attached to either the amino or the carboxyl group of an amino acid, and the nature of the chemical synthesis will dictate which reactive group will require a protecting group. Analogously, attachment of a protecting group to the 5'-hydroxyl group of a nucleoside during synthesis using for example, phosphate-triester coupling chemistry, prevents the 5'-hydroxyl of one nucleoside from reacting with the 3'-activated phosphate-triester of another.

Regardless of the specific use, protecting groups are employed to protect a moiety on a molecule from reacting with another reagent. Protecting groups of the present invention have the following characteristics: they prevent selected reagents from modifying the group to which they are attached; they are stable (that is, they remain attached to the molecule) to the synthesis reaction conditions; they are removable under conditions that do not adversely affect the remaining structure; and once removed, do not react appreciably with the surface or surface-bound oligomer. The selection of a suitable protecting group will depend, of course, on the chemical nature of the monomer unit and oligomer, as well as the specific reagents they are to protect against.

In a preferred embodiment, the protecting groups are photoactivatable. The properties and uses of photoreactive protecting compounds have been reviewed. See, McCray et al., *Ann. Rev. of Biophys. and Biophys. Chem.* (1989) 18:239-270, which is incorporated herein by reference. Preferably, the photosensitive protecting groups will be removable by radiation in the ultraviolet (UV) or visible portion of the electromagnetic spectrum. More preferably, the protecting groups will be removable by radiation in the near UV or visible portion of the spectrum. In some embodiments, however, activation may be performed by other methods such as localized heating, electron beam lithography, laser pumping, oxidation or reduction with microelectrodes, and the like. Sulfonyl compounds are suitable reactive groups for electron beam lithography. Oxidative or reductive removal is accomplished by exposure of the protecting group to an electric current source, preferably using microelectrodes directed to the predefined regions of the surface which are desired for activation. Other methods may be used in light of this disclosure.

Many, although not all, of the photoremovable protecting groups will be aromatic compounds that absorb near-UV and visible radiation. Suitable photoremovable protecting groups are described in, for example, McCray et al., Patchornik, *J. Amer. Chem. Soc.* (1970) 92:6333, and Amit et al., *J. Org. Chem.* (1974) 39:192, which are incorporated herein by reference.

A preferred class of photoremovable protecting groups has the general formula:

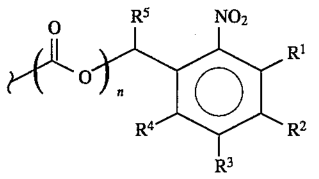

where $R^1$, $R^2$, $R^3$, and $R^4$ independently are a hydrogen atom, a lower alkyl, aryl, benzyl, halogen, hydroxyl, alkoxyl, thiol, thioether, amino, nitro, carboxyl, formate, formamido or phosphido group, or adjacent substituents (i.e., $R^1$-$R^2$, $R^2$-$R^3$, $R^3$-$R^4$) are substituted oxygen groups that together form a cyclic acetal or ketal; $R^5$ is a hydrogen atom, a alkoxyl, alkyl, hydrogen, halo, aryl, or alkenyl group, and n=0 or 1.

A preferred protecting group, 6-nitroveratryl (NV), which is used for protecting the carboxyl terminus of an amino acid or the hydroxyl group of a nucleotide, for example, is formed when $R^2$ and $R^3$ are each a methoxy group, $R^1$, $R^4$ and $R^5$ are each a hydrogen atom, and n=0:

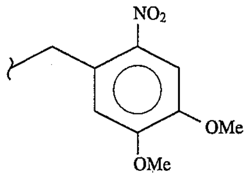

A preferred protecting group, 6-nitroveratryloxycarbonyl (NVOC), which is used to protect the amino terminus of an amino acid, for example, is formed when $R^2$ and $R^3$ are each a methoxy group, $R^1$, $R^4$ and $R^5$ are each a hydrogen atom, and n=1:

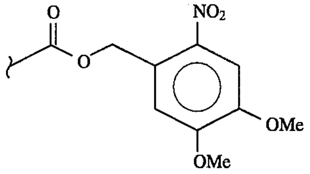

Another preferred protecting group, 6-nitropiperonyl (NP), which is used for protecting the carboxyl terminus of an amino acid or the hydroxyl group of a nucleotide, for example, is formed when $R^2$ and $R^3$ together form a methylene acetal, $R^1$, $R^4$ and $R^5$ are each a hydrogen atom, and n=0:

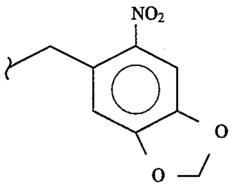

Another preferred protecting group, 6-nitropiperonyloxycarbonyl (NPOC), which is used to protect the amino terminus of an amino acid, for example, is formed when $R^2$ and $R^3$ together form a methylene acetal, $R^1$, $R^4$ and $R^5$ are each a hydrogen atom, and n=1:

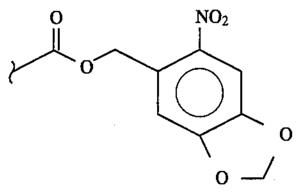

A most preferred protecting group, methyl-6-nitroveratryl (MeNV), which is used for protecting the carboxyl terminus of an amino acid or the hydroxyl group of a nucleotide, for example, is formed when $R^2$ and $R^3$ are each a methoxy group, $R^1$ and $R^4$ are each a hydrogen atom, $R^5$ is a methyl group, and n=0:

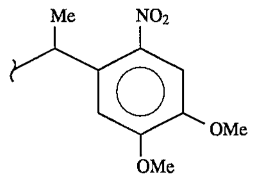

Another most preferred protecting group, methyl-6-nitroveratryloxycarbonyl (MeNVOC), which is used to protect the amino terminus of an amino acid, for example, is formed when $R^2$ and $R^3$ are each a methoxy group, $R^1$ and $R^4$ are each a hydrogen atom, $R^5$ is a methyl group, and n=1:

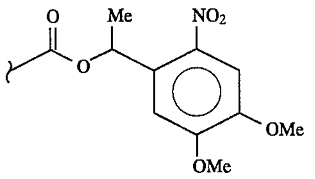

Another most preferred protecting group, methyl-6-nitropiperonyl (MeNP), which is used for protecting the carboxyl terminus of an amino acid or the hydroxyl group of a nucleotide, for example, is formed when $R^2$ and $R^3$ together form a methylene acetal, $R^1$ and $R^4$ are each a hydrogen atom, $R^5$ is a methyl group, and n=0:

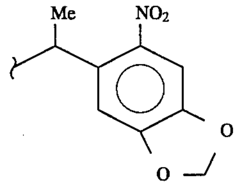

Another most preferred protecting group, methyl-6-nitropiperonyloxycarbonYl (MeNPOC), which is used to protect the amino terminus of an amino acid, for example, is formed when $R^2$ and $R^3$ together form a methylene acetal, $R^1$ and $R^4$ are each a hydrogen atom, $R^5$ is a methyl group, and n=1:

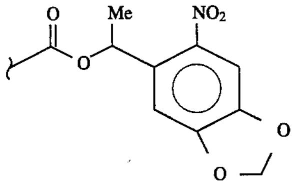

A protected amino acid having a photoactivatable oxycarbonyl protecting group, such NVOC or NPOC or their corresponding methyl derivatives, MeNVOC or MeNPOC, respectively, on the amino terminus is formed by acylating the amine of the amino acid with an activated oxycarbonyl ester of the protecting group. Examples of activated oxycarbonyl esters of NVOC and MeNVOC have the general formula:

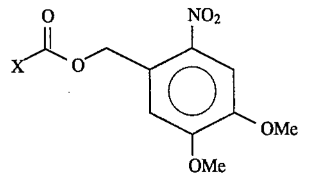

NVOC-X

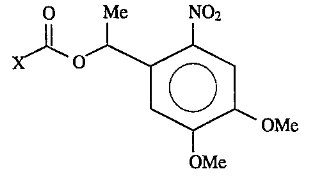

MeNVOC-X where X is halogen, mixed anhydride, phenoxy, p-nitrophenoxy, N-hydroxysuccinimide, and the like.

A protected amino acid or nucleotide having a photoactivatable protecting group, such as NV or NP or their corresponding methyl derivatives, MeNV or MeNP, respectively, on the carboxy terminus of the amino acid or 5'-hydroxy terminus of the nucleotide, is formed by acylating the carboxy terminus or 5'-OH with an activated benzyl derivative of the protecting group. Examples of activated benzyl derivatives of MeNV and MeNP have the general formula:

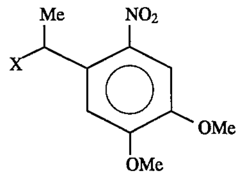

MeNV-X

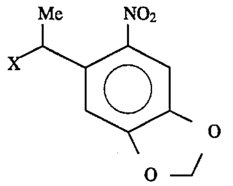

MeNP-X where X is halogen, hydroxyl, tosyl, mesyl, trifluormethyl, diazo, azido, and the like.

Another method for generating protected monomers is to react the benzylic alcohol derivative of the protecting group with an activated ester of the monomer. For example, to protect the carboxyl terminus of an amino acid, an activated ester of the amino acid is reacted with the alcohol derivative of the protecting group, such as 6-nitroveratrol (NVOH). Examples of activated esters suitable for such uses include halo-formate, mixed anhydride, imidazoyl formate, acyl halide, and also includes formation of the activated ester in situ the use of common reagents such as DCC and the like. See Atherton et al. for other examples of activated esters.

A further method for generating protected monomers is to react the benzylic alcohol derivative of the protecting group with an activated carbon of the monomer. For example, to protect the 5'-hydroxyl group of a nucleic acid, a derivative having a 5'-activated carbon is reacted with the alcohol derivative of the protecting group, such as methyl-6-nitropiperonol (MePyROH). Examples of nucleotides having activating groups attached to the 5'-hydroxyl group have the general formula:

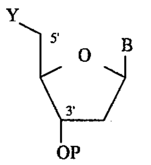

where Y is a halogen atom, a tosyl, mesyl, trifluoromethyl, azido, or diazo group, and the like.

Another class of preferred photochemical protecting groups has the formula:

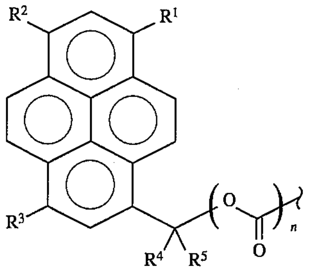

where $R^1$, $R^2$, and $R^3$ independently are a hydrogen atom, a lower alkyl, aryl, benzyl, halogen, hydroxyl, alkoxyl, thiol, thioether, amino, nitro, carboxyl, formate, formamido, sulfanates, sulfido or phosphido group, $R^4$ and $R^5$ independently are a hydrogen atom, an alkoxy, alkyl, halo, aryl, hydrogen, or alkenyl group, and n=0 or 1.

A preferred protecting group, 1-pyrenylmethyloxycarbonyl (PyROC), which is used to protect the amino terminus of an amino acid, for example, is formed when $R^1$ through $R^5$ are each a hydrogen atom and n=1:

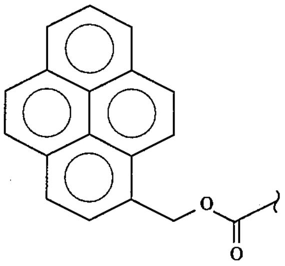

Another preferred protecting group, 1-pyrenylmethyl (PyR), which is used for protecting the carboxy terminus of an amino acid or the hydroxyl group of a nucleotide, for example, is formed when $R^1$ through $R^5$ are each a hydrogen atom and n=0:

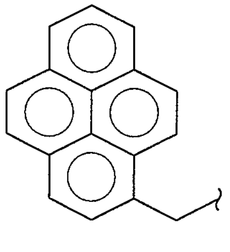

An amino acid having a pyrenylmethyloxycarbonyl protecting group on its amino terminus is formed by acylation of the free amine of amino acid with an activated oxycarbonyl ester of the pyrenyl protecting group. Examples of activated oxycarbonyl esters of PyROC have the general formula:

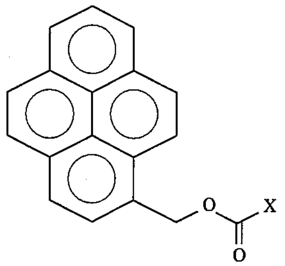

where X is halogen, or mixed anhydride, p-nitrophenoxy, or N-hydroxysuccinimide group, and the like.

A protected amino acid or nucleotide having a photoactivatable protecting group, such as PyR, on the carboxy terminus of the amino acid or 5'-hydroxy terminus of the nucleic acid, respectively, is formed by acylating the carboxy terminus or 5'-OH with an activated pyrenylmethyl derivative of the protecting group. Examples of activated pyrenylmethyl derivatives of PyR have the general formula:

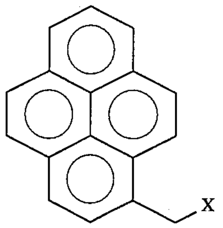

where X is a halogen atom, a hydroxyl, diazo, or azido group, and the like.

Another method of generating protected monomers is to react the pyrenylmethyl alcohol moiety of the protecting group with an activated ester of the monomer. For example, an activated ester of an amino acid can be reacted with the alcohol derivative of the protecting group, such as pyrenylmethyl alcohol (PyROH), to form the protected derivative of the carboxy terminus of the amino acid. Examples of activated esters include halo-formate, mixed anhydride, imidazoyl formate, acyl halide, and also includes formation of the activated ester in situ and the use of common reagents such as DCC and the like.

Clearly, many photosensitive protecting groups are suitable for use in the present invention.

In preferred embodiments, the substrate is irradiated to remove the photoremovable protecting groups and create regions having free reactive moieties and side products resulting from the protecting group. The removal rate of the protecting groups depends on the wavelength and intensity of the incident radiation, as well as the physical and chemical properties of the protecting group itself. Preferred protecting groups are removed at a faster rate and with a lower intensity of radiation. For example, at a given set of conditions, MeNVOC and MeNPOC are photolytically removed from the N-terminus of a peptide chain faster than their unsubstituted parent compounds, NVOC and NPOC, respectively.

Removal of the protecting group is accomplished by irradiation to liberate the reactive group and degradation products derived from the protecting group. Not wishing to be bound by theory, it is believed that irradiation of an NVOC- and MeNVOC-protected oligomers occurs by the following reaction schemes:

NVOC-AA →3,4-dimethoxy-6-nitrosobenzaldehyde+$CO_2$+AA

MeNVOC-AA→3,4-dimethoxy-6-nitrosoacetophenone+$CO_2$+AA where AA represents the N-terminus of the amino acid oligomer.

Along with the unprotected amino acid, other products are liberated into solution: carbon dioxide and a 2,3-dimethoxy-6-nitrosophenylcarbonyl compound, which can react with nucleophilic portions of the oligomer to form unwanted secondary reactions. In the case of an NVOC-protected amino acid, the degradation product is a nitrosobenzaldehyde, while the degradation product for the other is a nitrosophenyl ketone. For instance, it is believed that the product aldehyde from NVOC degradation reacts with free amines to form a Schiff base (imine) that affects the remaining polymer synthesis. Preferred photoremovable protecting groups react slowly or reversibly with the oligomer on the support.

Again not wishing to be bound by theory, it is believed that the product ketone from irradiation of a MeNVOC-protected oligomer reacts at a slower rate with nucleophiles on the oligomer than the product aldehyde from irradiation of the same NVOC-protected oligomer. Although not unambiguously determined, it is believed that this difference in reaction rate is due to the difference in general reactivity between aldehyde and ketones towards nucleophiles due to steric and electronic effects.

The photoremovable protecting groups of the present invention are readily removed. For example, the photolysis of N-protected L-phenylalanine in solution and having different photoremovable protecting groups was analyzed, and the results are presented in the following table:

TABLE

Photolysis of Protected L—Phe—OH

| Solvent | $t_{1/2}$ in seconds | | | |
|---|---|---|---|---|
| | NBOC | NVOC | MeNVOC | MeNPOC |
| Dioxane | 1288 | 110 | 24 | 19 |
| 5 mM $H_2SO_4$/Dioxane | 1575 | 98 | 33 | 22 |

The half life, $t_{1/2}$, is the time in seconds required to remove 50% of the starting amount of protecting group. NBOC is the 6-nitrobenzyloxycarbonyl group, NVOC is the 6-nitroveratryloxycarbonyl group, MeNVOC is the methyl-6-nitroveratryloxycarbonyl group, and MeNPOC is the methyl-6-nitropiperonyloxycarbonyl group. The photolysis was carried out in the indicated solvent with 362/364 nm-wavelength irradiation having an intensity of 10 $mW/cm^2$, and the concentration of each protected phenylalanine was 0.10 mM.

The table shows that deprotection of NVOC-, MeNVOC-, and MeNPOC-protected phenylalanine proceeded faster than the deprotection of NBOC. Furthermore, it shows that the deprotection of the two derivatives that are substituted on the benzylic carbon, MeNVOC and MeNPOC, were photolyzed at the highest rates in both dioxane and acidified dioxane.

1. Use of Photoremovable Groups During Solid-Phase Synthesis of Peptides

The formation of peptides on a solid-phase support requires the stepwise attachment of an amino acid to a substrate-bound growing chain. In order to prevent unwanted polymerization of the monomeric amino acid under the reaction conditions, protection of the amino terminus of the amino acid is required. After the monomer is coupled to the end of the peptide, the N-terminal protecting group is removed, and another amino acid is coupled to the chain. This cycle of coupling and deprotecting is continued for each amino acid in the peptide sequence. See Merrifield, *J. Am. Chem. Soc.* (1963) 85:2149, and Atherton et al., "Solid Phase Peptide Synthesis" 1989, IRL Press, London, both incorporated herein by reference for all purposes. As described above, the use of a photoremovable protecting group allows removal of selected portions of the substrate surface, via patterned irradiation, during the deprotection cycle of the solid phase synthesis. This selectively allows spatial control of the synthesis—the next amino acid is coupled only to the irradiated areas.

In one embodiment, the photoremovable protecting groups of the present invention are attached to an activated ester of an amino acid at the amino terminus:

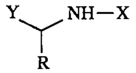

where R is the side chain of a natural or unnatural amino acid, X is a photoremovable protecting group, and Y is an activated carboxylic acid derivative. The photoremovable protecting group, X, is preferably NVOC, NPOC, PyROC, MeNVOC, MeNPOC, and the like as discussed above. The activated ester, Y, is preferably a reactive derivative having a high coupling efficiency, such as an acyl halide, mixed anhydride, N-hydroxysuccinimide ester, perfluorophenyl ester, or urethane protected acid, and the like. Other activated esters and reaction conditions are well known (See Atherton et al.).

2. Use of Photoremovable Groups During Solid-Phase Synthesis of Oligonucleotides The formation of oligonucleotides on a solid-phase support requires the stepwise attachment of a nucleotide to a substrate-bound growing oligomer. In order to prevent unwanted polymerization of the monomeric nucleotide under the reaction conditions, protection of the 5'-hydroxyl group of the nucleotide is required. After the monomer is coupled to the end of the oligomer, the 5'-hydroxyl protecting group is removed, and another nucleotide is coupled to the chain. This cycle of coupling and deprotecting is continued for each nucleotide in the oligomer sequence. See Gait, "Oligonucleotide Synthesis: A Practical Approach" 1984, IRL Press, London, incorporated herein by reference for all purposes. As described above, the use of a photoremovable protecting group allows removal, via patterned irradiation, of selected portions of the substrate surface during the deprotection cycle of the solid phase synthesis. This selectively allows spatial control of the synthesis—the next nucleotide is coupled only to the irradiated areas.

Oligonucleotide synthesis generally involves coupling an activated phosphorous derivative on the 3'-hydroxyl group of a nucleotide with the 5'-hydroxyl group of an oligomer bound to a solid support. Two major chemical methods exist to perform this coupling: the phosphate-triester and phosphoramidite methods (See Gait). Protecting groups of the present invention are suitable for use in either method.

In a preferred embodiment, a photoremovable protecting group is attached to an activated nucleotide on the 5'-hydroxyl group:

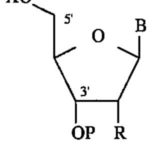

where B is the base attached to the sugar ring; R is a hydrogen atom when the sugar is deoxyribose or R is a hydroxyl group when the sugar is ribose; P represents an activated phosphorous group; and X is a photoremovable protecting group. The photoremovable protecting group, X, is preferably NV, NP, PyR, MeNV, MeNP, and the like as described above. The activated phosphorous group, P, is preferably a reactive derivative having a high coupling efficiency, such as a phosphate-triester, phosphoramidite or the like. Other activated phosphorous derivatives, as well as reaction conditions, are well known (See Gait).

E. Amino Acid N-Carboxy Anhydrides Protected With a Photoremovable Group

During Merrifield peptide synthesis, an activated ester of one amino acid is coupled with the free amino terminus of a substrate-bound oligomer. Activated esters of amino acids suitable for the solid phase synthesis include halo-formate, mixed anhydride, imidazoyl formate, acyl halide, and also includes formation of the activated ester in situ and the use of common reagents such as DCC and the like (See Atherton et al.). A preferred protected and activated amino acid has the general formula:

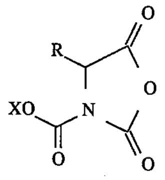

where R is the side chain of the amino acid and X is a photoremovable protecting group. This compound is a urethane-protected amino acid having a photoremovable protecting group attach to the amine. A more preferred activated amino acid is formed when the photoremovable protecting group has the general formula:

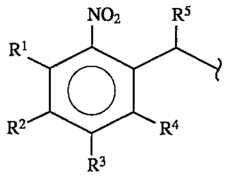

where $R^1$, $R^2$, $R^3$, and $R^4$ independently are a hydrogen atom a lower alkyl, aryl, benzyl, halogen, hydroxyl, alkoxyl, thiol, thioether, amino, nitro, carboxyl, formate, formamido or phosphido group, or adjacent substituents (i.e., $R^1$-$R^2$, $R^2$-$R^3$, $R^3$-$R^4$) are substituted oxygen groups that together form a cyclic acetal or ketal; and $R^5$ is a hydrogen atom, a alkoxyl, alkyl, hydrogen, halo, aryl, or alkenyl group.

A preferred activated amino acid is formed when the photoremovable protecting group is 6-nitroveratryloxycarbonyl. That is, $R^1$ and $R^4$ are each a hydrogen atom, $R^2$ and $R^3$ are each a methoxy group, and $R^5$ is a hydrogen atom. Another preferred activated amino acid is formed when the photoremovable group is 6-nitropiperonyl: $R^1$ and $R^4$ are each a hydrogen atom, $R^2$ and $R^3$ together form a methylene acetal, and $R^5$ is a hydrogen atom. Other protecting groups are possible. Another preferred activated ester is formed when the photoremovable group is methyl-6-nitroveratryl or methyl- 6-nitropiperonyl.

Another preferred activated amino acid is formed when the photoremovable protecting group has the general formula:

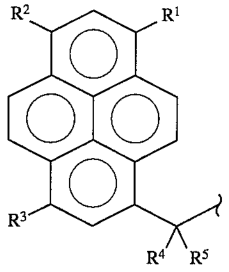

where $R^1$, $R^2$, and $R^3$ independently are a hydrogen atom, a lower alkyl, aryl, benzyl, halogen, hydroxyl, alkoxyl, thiol, thioether, amino, nitro, carboxyl, formate, formamido, sulfanates, sulfido or phosphido group, and $R^4$ and $R^5$ independently are a hydrogen atom, an alkoxy, alkyl, halo, aryl, hydrogen, or alkenyl group. The resulting compound is a urethane-protected amino acid having a pyrenylmethyloxycarbonyl protecting group attached to the amine. A more preferred embodiment is formed when $R^1$ through $R^5$ are each a hydrogen atom.

The urethane-protected amino acids having a photoremovable protecting group of the present invention are prepared by condensation of an N-protected amino acid with an acylating agent such as an acyl halide, anhydride, chloroformate and the like (See Fuller et al., U.S. Pat. No. 4,946,942 and Fuller et al., *J. Amer. Chem. Soc.* (1990) 112:7414–7416, both herein incorporated by reference for all purposes).

Urethane-protected amino acids having photoremovable protecting groups are generally useful as reagents during solid-phase peptide synthesis, and because of the spatially selectivity possible with the photoremovable protecting group, are especially useful for the spatially addressable peptide synthesis. These amino acids are difunctional: the urethane group first serves to activate the carboxy terminus for reaction with the amine bound to the surface and, once the peptide bond is formed, the photoremovable protecting group protects the newly formed amino terminus from further reaction. These amino acids are also highly reactive to nucleophiles, such as deprotected amines on the surface of the solid support, and due to this high reactivity, the solid-phase peptide coupling times are significantly reduced, and yields are typically higher.

IV. Data Collection

A. Data Collection System

Figure 11:
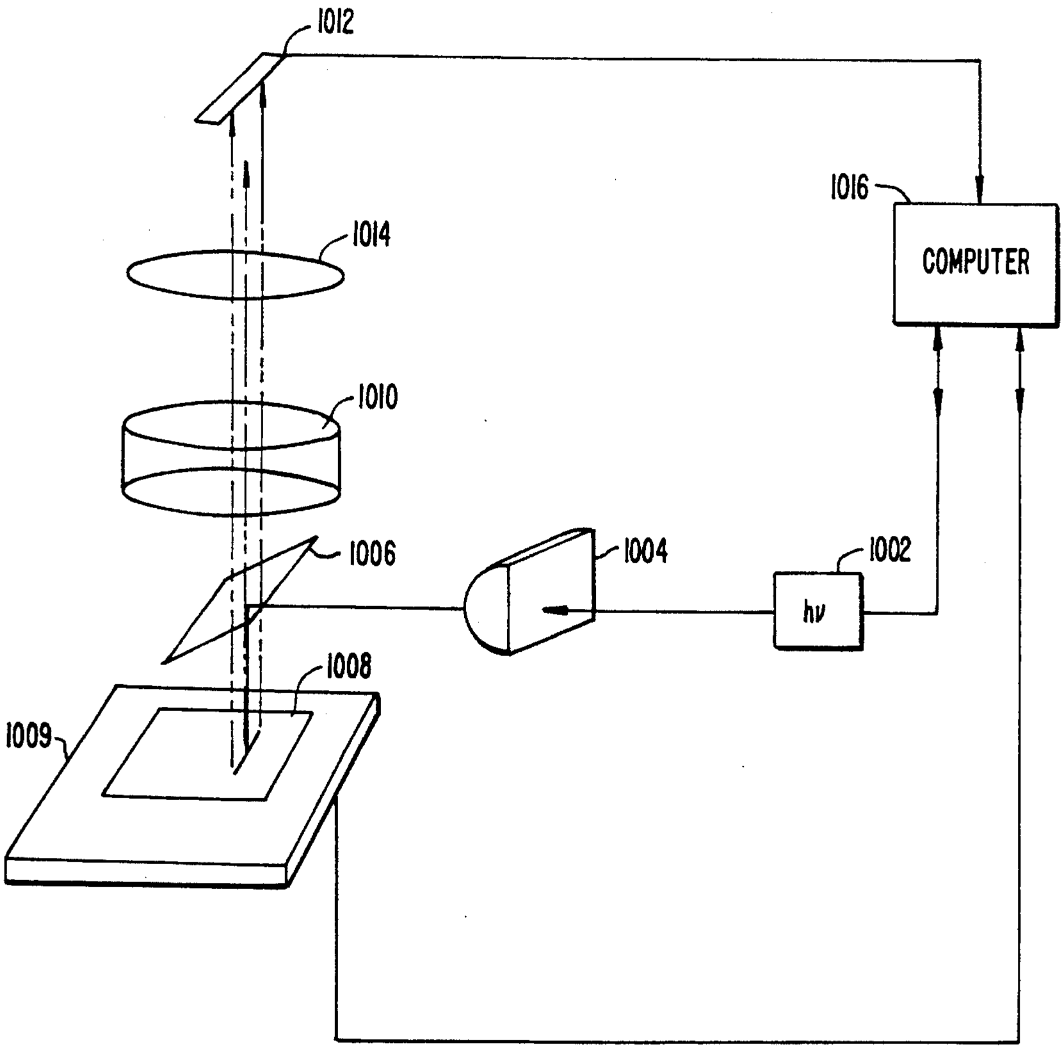
FIG. 11 schematically illustrates a data collection system.

Substrates prepared in accordance with the above description are used in one embodiment to determine which of the plurality of sequences thereon bind to a receptor of interest. FIG. 11 illustrates one embodiment of a device used to detect regions of a substrate which contain fluorescent markers. This device would be used, for example, to detect the presence or absence of a labeled receptor such as an antibody which has bound to a synthesized polymer on a substrate.

Light is directed at the substrate from a light source 1002 such as a laser light source of the type well known to those of skill in the art such as a model no. 2025 made by Spectra Physics. Light from the source is directed at a lens 1004 which is preferably a cylindrical lens of the type well known to those of skill in the art. The resulting output from the lens 1004 is a linear beam rather than a spot of light, resulting in the capability to detect data substantially simultaneously along a linear array of pixels rather than on a pixel-by-pixel basis. It will be understood that a cylindrical lens is used herein as an illustration of one technique for generating a linear beam of light on a surface, but that other techniques could also be utilized.

The beam from the cylindrical lens is passed through a dichroic mirror or prism (1006) and directed at the surface of the suitably prepared substrate 1008. Substrate 1008 is placed on an x-y translation stage 1009 such as a model no. PM500-8 made by Newport. Light at certain locations on the substrate will be fluoresced and transmitted along the path indicated by dashed lines back through the dichroic mirror, and focused with a suitable lens 1010 such as an f/1.4 camera lens on a linear detector 1012 via a variable f stop focusing lens 1014. Through use of a linear light beam, it becomes possible to generate data over a line of pixels (such as about 1 cm) along the substrate, rather than from individual points on the substrate. In alternative embodiments, light is directed at a 2-dimensional area of the substrate and fluoresced light detected by a 2-dimensional CCD array. Linear detection is preferred because substantially higher power densities are obtained.

Detector 1012 detects the amount of light fluoresced from the substrate as a function of position. According to one embodiment the detector is a linear CCD array of the type commonly known to those of skill in the art. The x-y translation stage, the light source, and the detector 1012 are all operably connected to a computer 1016 such as an IBM PC-AT or equivalent for control of the device and data collection from the CCD array.

In operation, the substrate is appropriately positioned by the translation stage. The light source is then illuminated, and intensity data are gathered with the computer via the detector.

Figure 12:
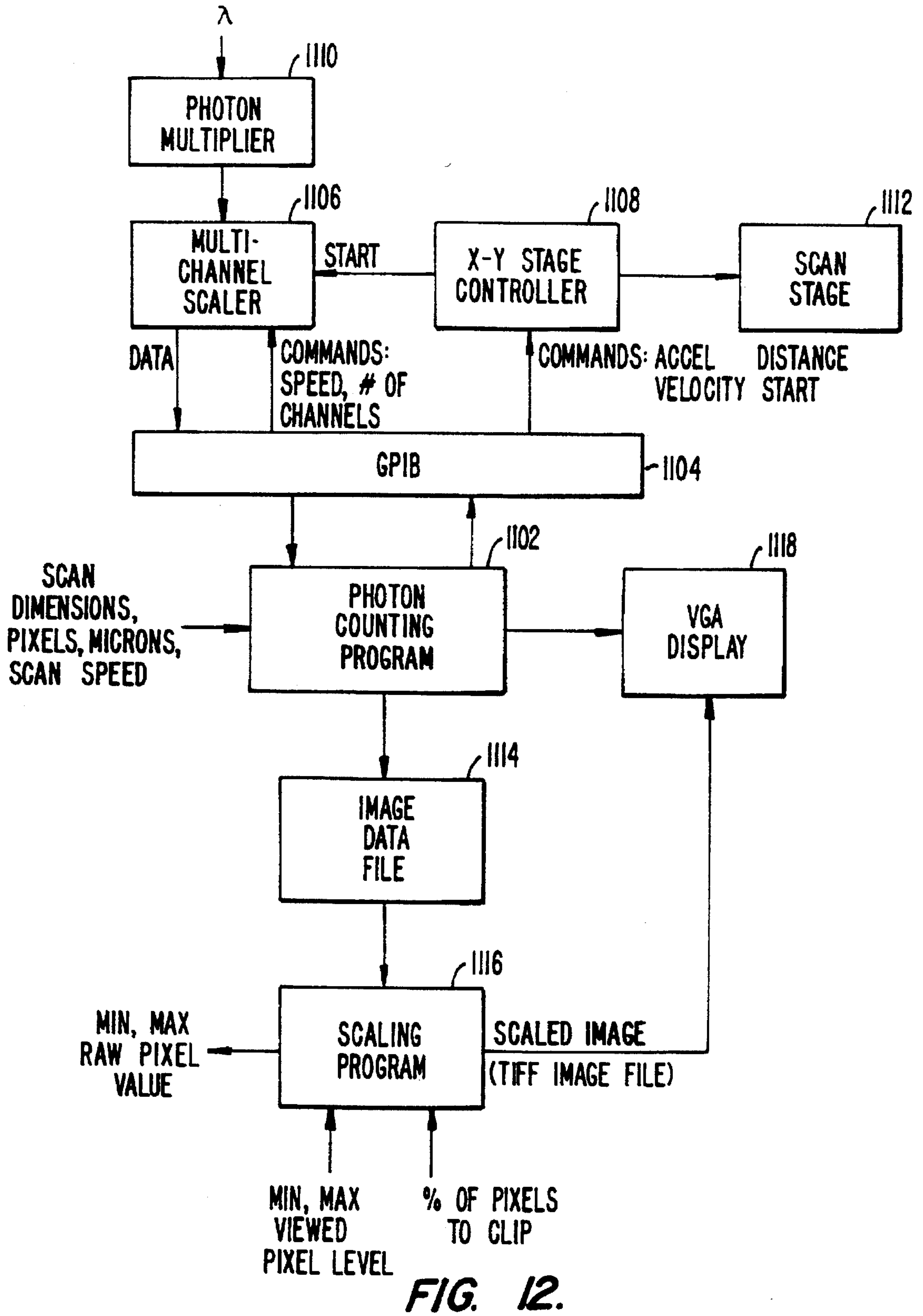
FIG. 12 is a block diagram illustrating the architecture of the data collection system.

FIG. 12 illustrates the architecture of the data collection system in greater detail. Operation of the system occurs under the direction of the photon counting program 1102 (photon), included herewith as Microfiche Appendix B. The user inputs the scan dimensions, the number of pixels or data points in a region, and the scan speed to the counting program. Via a GP1B bus 1104 the program (in an IBM PC compatible computer, for example) interfaces with a multichannel scaler 1106 such as a Stanford Research SR 430 and an x-y stage controller 1108 such as a PM500. The signal from the light from the fluorescing substrate enters a photon counter 1110, providing output to the scaler 1106. Data are output from the scaler indicative of the number of counts in a given region. After scanning a selected area, the stage controller is activated with commands for acceleration and velocity, which in turn drives the scan stage 1112 such as a PM500-A to another region.

Data are collected in an image data file 1114 and processed in a scaling program 1116, also included in Microfiche Appendix B. A scaled image is output for display on, for example, a VGA display 1118. The image is scaled based on an input of the percentage of pixels to clip and the minimum and maximum pixel levels to be viewed. The system outputs for use the min and max pixel levels in the raw data.

B. Data Analysis

The output from the data collection system is an array of data indicative of fluorescent intensity versus location on the substrate. The data are typically taken over regions substantially smaller than the area in which synthesis of a given polymer has taken place. Merely by way of example, if polymers were synthesized in squares on the substrate having dimensions of 500 microns by 500 microns, the data may be taken over regions having dimensions of 5 microns by 5 microns. In most preferred embodiments, the regions over which fluorescence data are taken across the substrate are less than about ½ the area of the regions in which individual polymers are synthesized, preferably less than 1/10 the area in which a single polymer is synthesized, and most preferably less than 1/100 the area in which a single polymer is synthesized. Hence, within any area in which a given polymer has been synthesized, a large number of fluorescence data points are collected.

A plot of number of pixels versus intensity for a scan of a cell when it has been exposed to, for example, a labeled antibody will typically take the form of a bell curve, but spurious data are observed, particularly at higher intensities. Since it is desirable to use an average of fluorescent intensity over a given synthesis region in determining relative binding affinity, these spurious data will tend to undesirably skew the data.

Accordingly, in one embodiment of the invention the data are corrected for removal of these spurious data points, and an average of the data points is thereafter utilized in determining relative binding efficiency.

Figure 13:
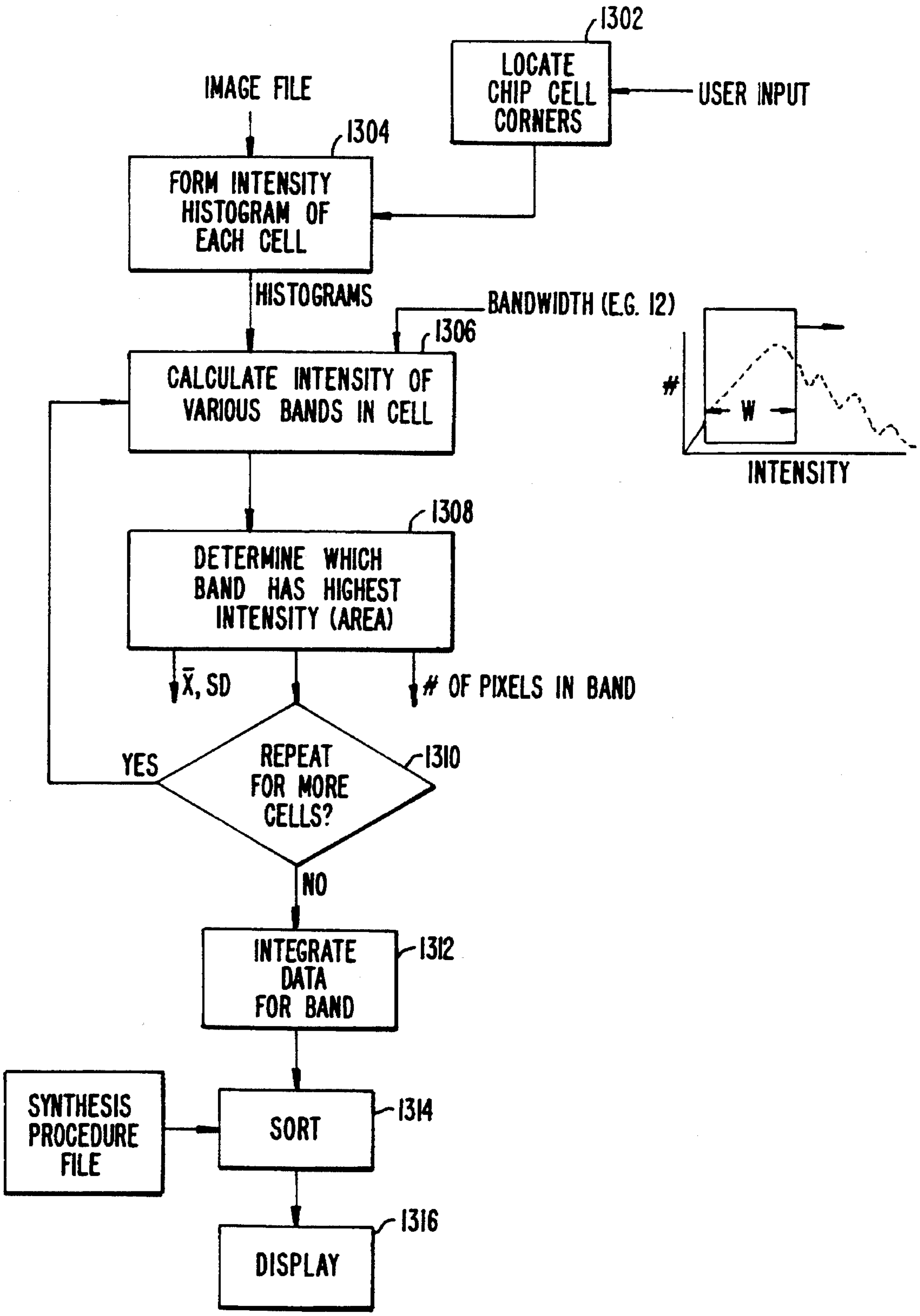
FIG. 13 is a flow chart illustrating operation of software for the data collection/analysis system.

FIG. 13 illustrates one embodiment of a system for removal of spurious data from a set of fluorescence data such as data used in affinity screening studies. A user or the system inputs data relating to the chip location and cell corners at step 1302. From this information and the image file, the system creates a computer representation of a histogram at step 1304, the histogram (at least in the form of a computer file) plotting number of data pixels versus intensity.

For each cell, a main data analysis loop is then performed. For each cell, at step 1306, the system calculates the total intensity or number of pixels for the bandwidth centered around varying intensity levels. For example, as shown in the plot to the right of step 1306, the system calculates the number of pixels within the band of width w. The system then "moves" this bandwidth to a higher center intensity, and again calculates the number of pixels in the bandwidth. This process is repeated until the entire range of intensities has been scanned, and at step 1308 the system determines which band has the highest total number of pixels. The data within this bandwidth are used for further analysis. Assuming the bandwidth is selected to be reasonably small, this procedure will have the effect of eliminating spurious data located at the higher intensity levels. The system then repeats at step 1310 if all cells have been evaluated, or repeats for the next cell.

At step 1312 the system then integrates the data within the bandwidth for each of the selected cells, sorts the data at step 1314 using the synthesis procedure file, and displays the data to a user on, for example, a video display or a printer.

V. Representative Applications

A. Oligonucleotide Synthesis

The generality of light directed spatially addressable parallel chemical synthesis is demonstrated by application to nucleic acid synthesis.

1. Example

Light activated formation of a thymidinecytidine dimer was carried out. A three dimensional representation of a fluorescence scan showing a checkerboard pattern generated by the light-directed synthesis of a dinucleotide is shown in FIG. 8. 5'-nitroveratryl thymidine was attached to a synthesis substrate through the 3' hydroxyl group. The nitroveratryl protecting groups were removed by illumination through a 500 mm checkerboard mask. The substrate was then treated with phosphoramidite activated 2'-deoxycytidine. In order to follow the reaction fluorometrically, the deoxycytidine had been modified with an FMOC protected aminohexyl linker attached to the exocyclic amine (5'-O-dimethoxytrityl-4-N-(6-N-fluorenylmethylcarbamoyl-hexylcarboxy)-2'-deoxycytidine). After removal of the FMOC protecting group with base, the regions which contained the dinucleotide were fluorescently labelled by treatment of the substrate with 1 mM FITC in DMF for one hour.

Figure 14:
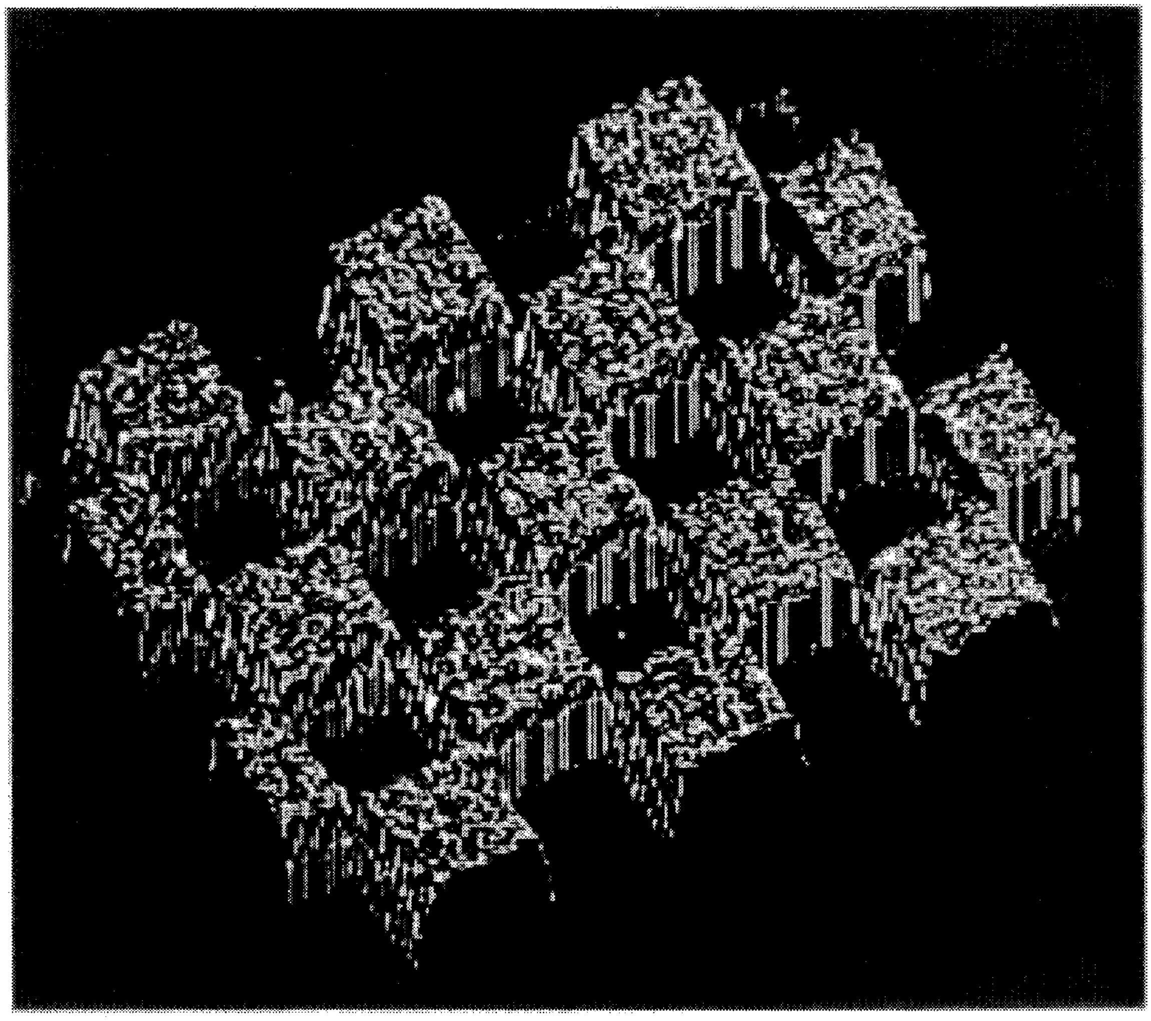
FIG. 14 illustrates a three-dimensional plot of intensity versus position for light directed synthesis of a dinucleotide.

The three-dimensional representation of the fluorescent intensity data in FIG. 14 clearly reproduces the checkerboard illumination pattern used during photolysis of the substrate. This result demonstrates that oligonucleotides as well as peptides can be synthesized by the light-directed method.

VI. Conclusion

The inventions herein provide a new approach for the simultaneous synthesis of a large number of compounds. The method can be applied whenever one has chemical building blocks that can be coupled in a solidphase format, and when light can be used to generate a reactive group.

The above description is illustrative and not restrictive. Many variations of the invention will become apparent to those of skill in the art upon review of this disclosure. Merely by way of example, while the invention is illustrated primarily with regard to peptide and nucleotide synthesis, the invention is not so limited. The scope of the invention should, therefore, be determined not with reference to the above description, but instead should be determined with reference to the appended claims along with their full scope of equivalents.

What is claimed is:

1. A compound comprising the following structure:

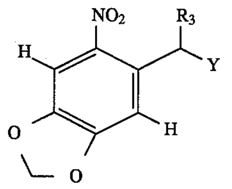

wherein Y is the C-5' oxygen group of a deoxyribonucleic acid; and $R^3$ is alkyl.

2. The compound of claim 1, wherein $R^3$ is methyl.

3. The compound of claim 1 having the formula:

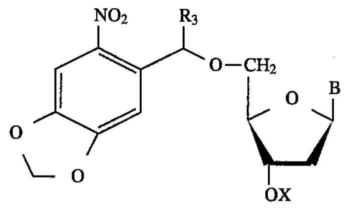

wherein B is selected from the group consisting of adenyl, guanyl, cytidyl, thymidyl, and uridyl; and X is hydrogen, a solid support, an oligonucleotide or an activated phosphorous group selected from the group consisting of phosphotriester and phosphoramidite.

4. The compound of claim 3, wherein X is a solid support.

5. The compound of claim 4, wherein B is adenyl.

6. The compound of claim 4, wherein B is guanyl.

7. The compound of claim 4, wherein B is cytidyl.

8. The compound of claim 4, wherein B is thymidyl.

9. The compound of claim 4, wherein B is uridyl.

10. The compound of claim 4, wherein $R^3$ is methyl.

11. The compound of claim 10, wherein B is adenyl.

12. The compound of claim 10, wherein B is guanyl.

13. The compound of claim 10, wherein B is cytidyl.

14. The compound of claim 10, wherein B is thymidyl.

15. The compound of claim 10, wherein B is uridyl.

16. The compound of claim 3, wherein X is an oligonucleotide.

17. The compound of claim 16, wherein $R^3$ is methyl.

18. The compound of claim 17, wherein B is adenyl.

19. The compound of claim 17, wherein B is guanyl.

20. The compound of claim 17, wherein B is cytidyl.

21. The compound of claim 17, wherein B is thymidyl.

22. The compound of claim 17, wherean B is uridyl.

23. The compound of claim 16, wherean said oligonucleotide is attached to a synthesis substrate.

24. The compound of claim 23, wherein $R^3$ is methyl.

25. The compound of claim 23, wherein B is adenyl.

26. The compound of claim 23, wherein B is guanyl.

27. The compound of claim 23, wherean B is cytidyl.

28. The compound of claim 23, wherein B is thymidyl.

29. The compound of claim 23, wherean B is uridyl.

30. The compound of claim 3, wherein X is selected from the group consisting of phosphatetriester and phosphoramidite.

31. The compound of claim 30, wherein B is adenyl.

32. The compound of claim 30, wherein B is guanyl.

33. The compound of claim 30, wherein B is thymidyl.

34. The compound of claim 30, wherein B is cytidyl.

35. The compound of claim 30, wherein B is uridyl.

* * * * *

UNITED STATES PATENT AND TRADEMARK OFFICE

CERTIFICATE OF CORRECTION

PATENT NO. : 5,489,678

DATED : Febuary 6, 1996

INVENTOR(S) : Stephen P.A. Fodor, Christopher P. Holmes, and Dennis W. Solas

It is certified that error appears in the above-identified patent and that said Letters Patent is hereby corrected as shown below:

On title page, item [75], inventors should read as follows:

Inventors: Stephen P.A. Fodor, Palo Alto; Christopher P. Holmes, Sunnyvale; Dennis W. Solas, San Francisco, all of Calif.

Signed and Sealed this

Fifth Day of November, 1996

*Attest:*

BRUCE LEHMAN

*Attesting Officer*

*Commissioner of Patents and Trademarks*

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Tyr Gly Gly Phe Leu
1               5
```

( 2 ) INFORMATION FOR SEQ ID NO:2:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

```
Pro Gly Gly Phe Leu
1               5
```

( 2 ) INFORMATION FOR SEQ ID NO:3:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

```
Tyr Gly Ala Gly Phe
1               5
```

( 2 ) INFORMATION FOR SEQ ID NO:4:

( i ) SEQUENCE CHARACTERISTICS:
( A ) LENGTH: 6 amino acids
( B ) TYPE: amino acid
( C ) STRANDEDNESS: single
( D ) TOPOLOGY: linear -continued ( i i ) MOLECULE TYPE: peptide ( x i ) SEQUENCE DESCRIPTION: SEQ ID NO:4:

Tyr Gly Ala Phe Leu Ser
1 5

( 2 ) INFORMATION FOR SEQ ID NO:5:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:5:

Tyr Gly Ala Phe Ser
1 5

( 2 ) INFORMATION FOR SEQ ID NO:6:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:6:

Tyr Gly Ala Phe Leu
1 5

( 2 ) INFORMATION FOR SEQ ID NO:7:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:7:

Tyr Gly Gly Phe Leu Ser
1 5

( 2 ) INFORMATION FOR SEQ ID NO:8:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

Tyr Gly Ala Phe
1

( 2 ) INFORMATION FOR SEQ ID NO:9:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:9:

Tyr Gly Ala Leu Ser
1 5

( 2 ) INFORMATION FOR SEQ ID NO:10:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:10:

Tyr Gly Gly Phe Ser
1 5

( 2 ) INFORMATION FOR SEQ ID NO:11:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:11:

Tyr Gly Ala Leu
1

( 2 ) INFORMATION FOR SEQ ID NO:12:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

Tyr Gly Ala Phe Leu Phe
1 5

( 2 ) INFORMATION FOR SEQ ID NO:13:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:13:

Tyr Gly Ala Phe Phe
1 5

( 2 ) INFORMATION FOR SEQ ID NO:14:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:14:

Tyr Gly Gly Leu Ser
1 5

( 2 ) INFORMATION FOR SEQ ID NO:15:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:15:

Tyr Gly Gly Phe Leu
1 5

( 2 ) INFORMATION FOR SEQ ID NO:16:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:16:

Tyr Gly Ala Phe Ser Phe
1 5

( 2 ) INFORMATION FOR SEQ ID NO:17:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:17:

Tyr Gly Ala Phe Leu Ser Phe
1 5

( 2 ) INFORMATION FOR SEQ ID NO:18:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:18:

Tyr Gly Ala Phe Met Gln
1 5

( 2 ) INFORMATION FOR SEQ ID NO:19:

( i ) SEQUENCE CHARACTERISTICS:
( A ) LENGTH: 5 amino acids
( B ) TYPE: amino acid
( C ) STRANDEDNESS: single
( D ) TOPOLOGY: linear -continued ( i i ) MOLECULE TYPE: peptide ( x i ) SEQUENCE DESCRIPTION: SEQ ID NO:19:

Tyr Gly Ala Phe Met
1 5

( 2 ) INFORMATION FOR SEQ ID NO:20:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:20:

Tyr Gly Ala Phe Gln
1 5

( 2 ) INFORMATION FOR SEQ ID NO:21:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:21:

Tyr Gly Gly Phe Met
1 5